US011786688B2

(12) United States Patent
Walls et al.

(10) Patent No.: US 11,786,688 B2
(45) Date of Patent: Oct. 17, 2023

(54) HEADGEAR ASSEMBLY FOR BREATHING INTERFACE

(71) Applicant: Fisher & Paykel Healthcare Limited, Auckland (NZ)

(72) Inventors: Bruce Michael Walls, Auckland (NZ); Rex Gordon Faithfull, Auckland (NZ); Wen Dong Huang, Auckland (NZ); Arvin San Jose Gardiola, Auckland (NZ); Jeremy Owen Young, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 473 days.

(21) Appl. No.: 16/036,567

(22) Filed: Jul. 16, 2018

(65) Prior Publication Data

US 2018/0318541 A1 Nov. 8, 2018

Related U.S. Application Data

(63) Continuation of application No. 15/037,304, filed as application No. PCT/IB2014/066374 on Nov. 27, 2014, now Pat. No. 10,039,894.

(60) Provisional application No. 61/990,479, filed on May 8, 2014, provisional application No. 61/909,936, filed on Nov. 27, 2013.

(51) Int. Cl.
*A61M 16/06* (2006.01)
*A61M 16/08* (2006.01)

(52) U.S. Cl.
CPC .... *A61M 16/0683* (2013.01); *A61M 16/0816* (2013.01); *A61M 16/0666* (2013.01)

(58) Field of Classification Search
CPC ....... A61F 9/02–068; A63B 33/00–008; B63C 11/12–16; G02C 3/02
See application file for complete search history.

(56) References Cited

U.S. PATENT DOCUMENTS

| 2,979,794 A | * | 4/1961 | De Bartolo | F16L 3/233 24/17 R |
| 3,040,741 A | | 6/1962 | Carolan | |
| 3,416,521 A | | 12/1968 | Hamlin | |

(Continued)

FOREIGN PATENT DOCUMENTS

| JP | D1464190 | 2/2013 |
| KR | 100828240 B1 | 5/2008 |

(Continued)

OTHER PUBLICATIONS

Australian Examination Report for Application No. 2017245368 dated Sep. 17, 2019, 7 pages.

(Continued)

*Primary Examiner* — Rachel T Sippel
(74) *Attorney, Agent, or Firm* — Knobbe Martens Olson and Bear, LLP

(57) ABSTRACT

An interface and headgear assembly includes a headgear assembly. The headgear assembly has a first strap configured to connect to the interface. A crown strap can be adjusted along a length of the first strap. In some configurations, the crown strap has a first portion and a second portion that are adjustably connected. The crown strap can be removably connected to the first strap using bridge regions of the first portion and the second portion.

21 Claims, 40 Drawing Sheets

(56) References Cited

U.S. PATENT DOCUMENTS

| | | | |
|---|---|---|---|
| 3,599,635 A | 8/1971 | Ansite | |
| 3,850,168 A | 11/1974 | Ferguson et al. | |
| 4,915,106 A * | 4/1990 | Aulgur | A62B 18/084 |
| | | | 128/205.24 |
| D335,367 S | 5/1993 | Mieskoski | |
| 5,394,568 A | 3/1995 | Brostrom et al. | |
| 5,517,986 A | 5/1996 | Starr et al. | |
| 5,720,040 A * | 2/1998 | Simone | A42B 1/247 |
| | | | 2/10 |
| 5,724,965 A * | 3/1998 | Handke | A61M 16/06 |
| | | | 128/205.25 |
| 6,119,694 A | 9/2000 | Correa et al. | |
| D496,726 S | 9/2004 | Amarasinghe et al. | |
| D532,511 S | 11/2006 | Amarasinghe | |
| D532,512 S | 11/2006 | Amarasinghe | |
| D536,092 S | 1/2007 | Amarasinghe | |
| D540,940 S | 4/2007 | Amarasinghe et al. | |
| D542,912 S | 5/2007 | Gunaratnam et al. | |
| D546,441 S | 7/2007 | Hitchcock et al. | |
| D561,332 S | 2/2008 | Amarasinghe et al. | |
| D612,933 S | 3/2010 | Prentice et al. | |
| D653,748 S | 2/2012 | Henry et al. | |
| D656,231 S | 3/2012 | Henry et al. | |
| D668,000 S | 9/2012 | Folkesson et al. | |
| D668,328 S | 10/2012 | Hill et al. | |
| D691,257 S | 10/2013 | Siew et al. | |
| D692,554 S | 10/2013 | Siew et al. | |
| D696,767 S | 12/2013 | Scheiner et al. | |
| D704,329 S | 5/2014 | Collazo et al. | |
| D706,413 S | 6/2014 | Veliss et al. | |
| D709,181 S | 7/2014 | Henry et al. | |
| 8,839,791 B2 | 9/2014 | Allum et al. | |
| D723,159 S | 2/2015 | Whitfield | |
| 8,985,115 B2 | 3/2015 | Baecke et al. | |
| D729,381 S | 5/2015 | Himes et al. | |
| D737,953 S | 9/2015 | Wells et al. | |
| D746,436 S | 12/2015 | Guney et al. | |
| D747,460 S | 1/2016 | Hogea et al. | |
| D770,036 S | 10/2016 | Walls et al. | |
| D771,239 S | 11/2016 | Walls et al. | |
| D787,661 S | 5/2017 | Edwards | |
| D797,921 S | 9/2017 | Huang et al. | |
| D815,728 S | 4/2018 | Walls et al. | |
| D822,194 S | 7/2018 | Walls et al. | |
| 10,039,894 B2 | 8/2018 | Walls et al. | |
| 10,080,856 B2 | 9/2018 | McLaren et al. | |
| D848,607 S | 5/2019 | Walls et al. | |
| D849,930 S | 5/2019 | Walls et al. | |
| D854,756 S | 7/2019 | Hovan et al. | |
| D854,758 S | 7/2019 | Rosca et al. | |
| D858,746 S | 9/2019 | Lee et al. | |
| D867,577 S | 11/2019 | Walls et al. | |
| D870,977 S | 12/2019 | Berggren et al. | |
| D875,242 S | 2/2020 | Gordon et al. | |
| D876,616 S | 2/2020 | Prentice et al. | |
| D879,287 S | 3/2020 | Walls et al. | |
| D892,305 S | 8/2020 | Walls et al. | |
| D987,068 S | 5/2023 | Walls et al. | |
| 2002/0011248 A1 | 1/2002 | Hansen et al. | |
| 2003/0196658 A1 | 10/2003 | Ging et al. | |
| 2004/0112377 A1 | 6/2004 | Amarasinghe et al. | |
| 2004/0226566 A1 | 11/2004 | Gunaratnam et al. | |
| 2005/0268914 A1 * | 12/2005 | Paoluccio | A61M 16/06 |
| | | | 128/205.25 |
| 2006/0081252 A1 | 4/2006 | Wood | |
| 2007/0163600 A1 | 7/2007 | Hoffman | |
| 2008/0190432 A1 | 8/2008 | Blochlinger et al. | |
| 2009/0044808 A1 | 2/2009 | Guney et al. | |
| 2009/0095298 A1 | 4/2009 | Gunaratnam et al. | |
| 2009/0250065 A1 | 10/2009 | Omura et al. | |
| 2010/0037897 A1 | 2/2010 | Wood | |
| 2010/0224109 A1 | 9/2010 | Meng | |
| 2010/0224199 A1 | 9/2010 | Smith et al. | |
| 2010/0229868 A1 | 9/2010 | Rummery et al. | |
| 2010/0258136 A1 | 10/2010 | Doherty et al. | |
| 2011/0000492 A1 | 1/2011 | Veliss et al. | |
| 2011/0146685 A1 | 6/2011 | Allan et al. | |
| 2011/0197341 A1 | 8/2011 | Formica et al. | |
| 2011/0232649 A1 | 9/2011 | Collazo et al. | |
| 2011/0253143 A1 | 10/2011 | Ho et al. | |
| 2011/0259335 A1 | 10/2011 | Sullivan | |
| 2012/0067349 A1 | 3/2012 | Barlow et al. | |
| 2012/0090622 A1 | 4/2012 | Chang | |
| 2012/0138060 A1 | 6/2012 | Barlow | |
| 2012/0174922 A1 | 7/2012 | Virr et al. | |
| 2012/0222680 A1 | 9/2012 | Eves et al. | |
| 2013/0042871 A1 | 2/2013 | Chang | |
| 2013/0186403 A1 | 7/2013 | Chang | |
| 2013/0199537 A1 | 8/2013 | Formica et al. | |
| 2013/0220327 A1 | 8/2013 | Barlow et al. | |
| 2014/0000614 A1 | 1/2014 | Chang | |
| 2014/0264975 A1 | 9/2014 | Bath et al. | |
| 2014/0283843 A1 | 9/2014 | Eves et al. | |
| 2015/0151071 A1 | 6/2015 | Von Moger et al. | |
| 2015/0199479 A1 | 7/2015 | Semen et al. | |
| 2015/0224274 A1 | 8/2015 | Siew et al. | |
| 2015/0290415 A1 | 10/2015 | Dunn et al. | |
| 2015/0335848 A1 * | 11/2015 | Eury | A61M 16/0057 |
| | | | 128/205.25 |
| 2016/0051784 A1 | 2/2016 | Eury et al. | |
| 2016/0151596 A1 | 6/2016 | Slight et al. | |
| 2016/0166792 A1 | 6/2016 | Allan et al. | |
| 2016/0166793 A1 | 6/2016 | McLaren et al. | |
| 2017/0080173 A1 | 3/2017 | Barlow et al. | |
| 2017/0119988 A1 | 5/2017 | Allan et al. | |
| 2018/0078725 A1 | 3/2018 | Richardson et al. | |
| 2018/0304036 A1 | 10/2018 | Huang et al. | |
| 2018/0318541 A1 | 11/2018 | Walls et al. | |
| 2019/0030272 A1 | 1/2019 | Graham et al. | |
| 2019/0298957 A1 | 10/2019 | McAuley et al. | |
| 2019/0298959 A1 | 10/2019 | Barlow et al. | |
| 2019/0351172 A1 | 11/2019 | Formica et al. | |
| 2020/0023153 A1 | 1/2020 | Chou et al. | |

FOREIGN PATENT DOCUMENTS

| | | |
|---|---|---|
| WO | WO 2007/041786 A1 | 4/2007 |
| WO | WO 2009/059353 A1 | 5/2009 |
| WO | WO 2011/060479 A1 | 5/2011 |
| WO | WO 2012/045127 A1 | 4/2012 |
| WO | WO 2013/082649 | 6/2013 |
| WO | WO 2014/025267 | 2/2014 |
| WO | WO 2014/175753 A1 | 10/2014 |

OTHER PUBLICATIONS

Reason for Rejection from Examination Report [Partial Translation], Japanese Design Application No. 2014-011228.
Australian Examination Report for Australian patent application 2017245368; dated Sep. 27, 2018; 3 pages.
Extended Search report in European Application No. 19157638.8 dated Aug. 16, 2019 in 7 pages.
Australian Examination Report; dated Jul. 8, 2016; 5 pages.
International Preliminary Report on Patentability; PCT/IB2014/066374; dated Jun. 9, 2016; 5 page.
International Search Report; PCT/IB2014/066374; dated Feb. 16, 2015; 3 pages.
Supplementary Search Report in European Application No. 14865246.4 dated Jun. 16, 2017 in 7 pages.
Australian Examination Report for Application No. 2019232901 dated Oct. 13, 2020, 4 pages.

* cited by examiner

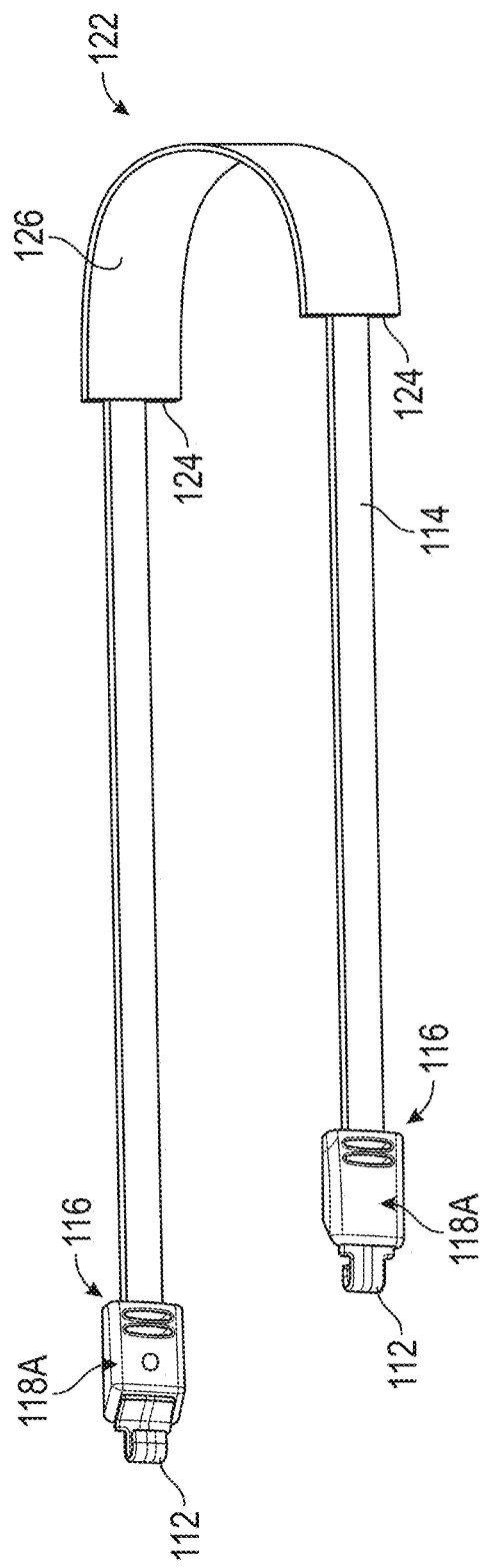
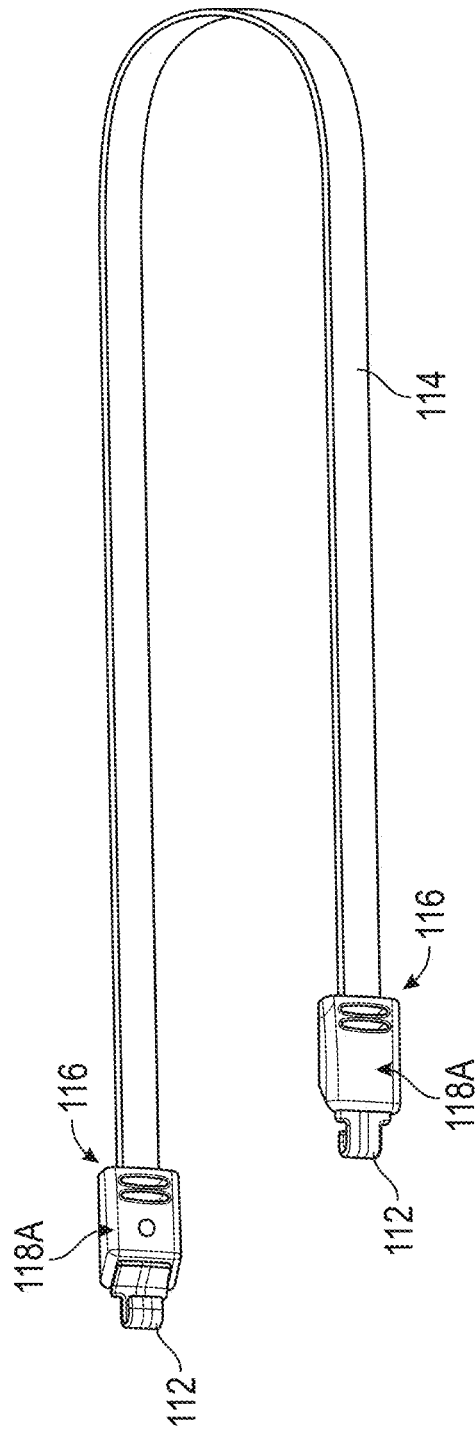
FIGURE 14
FIGURE 15

HEADGEAR ASSEMBLY FOR BREATHING INTERFACE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field

The present disclosure generally relates to headgear for respiratory devices, such as breathing masks. More particularly, the present disclosure relates to such headgear in which a strap extends circumferentially around a head.

Description of the Related Art

Headgear is used to secure an interface or breathing mask to the face of the user. The headgear can have any number of configurations. In general, the headgear is used to apply a force vector to the interface that opposes the forces generated by the interface while supplying breathing gases to the user. Not all users, however, have the same experience with any single form of headgear and, from time to time, any individual user may wish to change the user experience with the headgear being used by the user.

SUMMARY

Thus, it is an object of the disclosure to provide patients with a headgear assembly that might be easier to use or that is easily reconfigurable, or at least provide the public with a useful choice.

In some configurations, an interface and headgear assembly include an interface comprising a frame and a seal supported by the frame. A headgear assembly is removably connected to the interface. The headgear includes a first strap configured to connect at a first end to the interface and at a second end to the interface. A crown strap is connected to the first strap. The crown strap comprises a first bridge region and a second bridge region. The first bridge region defines a first passage that receives the first strap and the second bridge region defines a second passage that receives the first strap. Each of the first bridge region and the second bridge region is adjustable in position relative to the first strap.

In some configurations, each of the first bridge region and the second bridge region comprises multiple supporting components configured to secure the first bridge region and the second bridge region, respectively, to the first strap.

In some configurations, the supporting components comprise a first loop and a second loop configured to receive the strap of the interface and headgear assembly.

In some configurations, each of the first and second loops is an interrupted loop.

In some configurations, each of the first and second loops comprises an upper portion and a lower portion defining a slot therebetween.

In some configurations, a width of a passageway defined by each of the first and second loops is smaller at the upper portion than at a lower portion.

In some configurations, the assembly further comprises at least one medial member positioned between the first loop and the second loop and extending vertically upward from a lower lip of the first bridge region.

In some configurations, the at least one medial member supports the first strap at a relatively higher position than a position of the first strap at the first and second loops.

In some configurations, the at least one medial member comprises a lower medial member and an upper medial member and the first strap can be engaged with either of the lower or upper medial members to adjust an effective length of the first strap.

In some configurations, the crown strap comprises a first strap region and a second strap region, the first strap region and the second strap region being removably coupled together.

In some configurations, the first strap region and the second strap region are coupled by an adjustment mechanism.

In some configurations, the adjustment mechanism comprises a plurality of apertures and one or more posts that are selectively engageable with the plurality of apertures.

In some configurations, the adjustment mechanism comprises two or more slots and a plurality of ridges that are selectively engageable with the one or more slots.

In some configurations, the adjustment mechanism comprises one or more slots and one or more wedges or flaps that are selectively engageable with the one or more slots.

In some configurations, the first strap is constructed from a stretchable material.

In some configurations, the first strap is a tubular-knitted elastic strap.

In some configurations, the crown strap is constructed from a substantially non-stretchable material.

In some configurations, at least a strap region of the crown strap is constructed from a flexible material.

In some configurations, the material of the strap region has sufficient rigidity such that it is capable of substantially maintaining its shape.

In some configurations, the assembly comprises a sleeve on the first strap.

In some configurations, a surface of the sleeve that contacts a user in use comprises grip-enhancing features.

In some configurations, a removable crown strap assembly is removably connected to the first strap.

In some configurations, the removable crown strap assembly comprises a first portion and a second portion.

In some configurations, the first portion and the second portion can be connected with an adjustment mechanism.

In some configurations, the first portion comprises a first strap region and a first bridge region and the second portion comprises a second strap region and a second bridge region.

In some configurations, the first bridge region defines a first passage that removably receives the first strap and the second bridge region defines a second passage that removably receives the first strap.

In some configurations, an interface and headgear assembly can be provided. The interface can comprise a frame and a seal supported by the frame. A headgear assembly can be removably connected to the interface. The headgear can comprise a first strap configured to connect at a first end to the interface and at a second end to the interface. A removable crown strap assembly can be removably connected to the first strap. The removable crown strap assembly comprises a first portion and a second portion. The first portion and the second portion can be connected with an adjustment mechanism. The first portion comprises a first strap region and a first bridge region and the second portion comprises a second strap region and a second bridge region. The first bridge region defines a first passage that removably receives the first strap and the second bridge region defines a second passage that removably receives the first strap.

In some configurations, a removable crown strap assembly can be configured for use with an interface and headgear assembly. The removable crown strap assembly comprises a first bridge region and a second bridge region configured to receive a strap of the interface and headgear assembly.

In some such configurations, the first bridge region comprises multiple supporting components configured to secure the first bridge region to the strap of the interface and headgear assembly. In some such configurations, the supporting components comprise a first interrupted loop and a second interrupted loop configured to receive the strap of the interface and headgear assembly. In some such configurations, a medial member is positioned between the first interrupted loop and the second interrupted loop and extends vertically upward from a lower lip of the first bridge region. In some such configurations, the removable crown strap assembly comprises a first strap region and a second strap region with the first strap region and the second strap region being removably coupled together. In some such configurations, the first strap region and the second strap region are coupled by an adjustment mechanism.

BRIEF DESCRIPTION OF THE DRAWINGS

These and other features, aspects and advantages of the present disclosure will now be described with reference to the drawings of preferred embodiments, which embodiments are intended to illustrate and not to limit the disclosure, and in which figures:

FIG. 14 is a side view of a rear strap of the headgear of FIG. 1A.

FIG. 15 is a side view of the rear strap of FIG. 14 with a rear sleeve removed.

DETAILED DESCRIPTION

Figure 1:
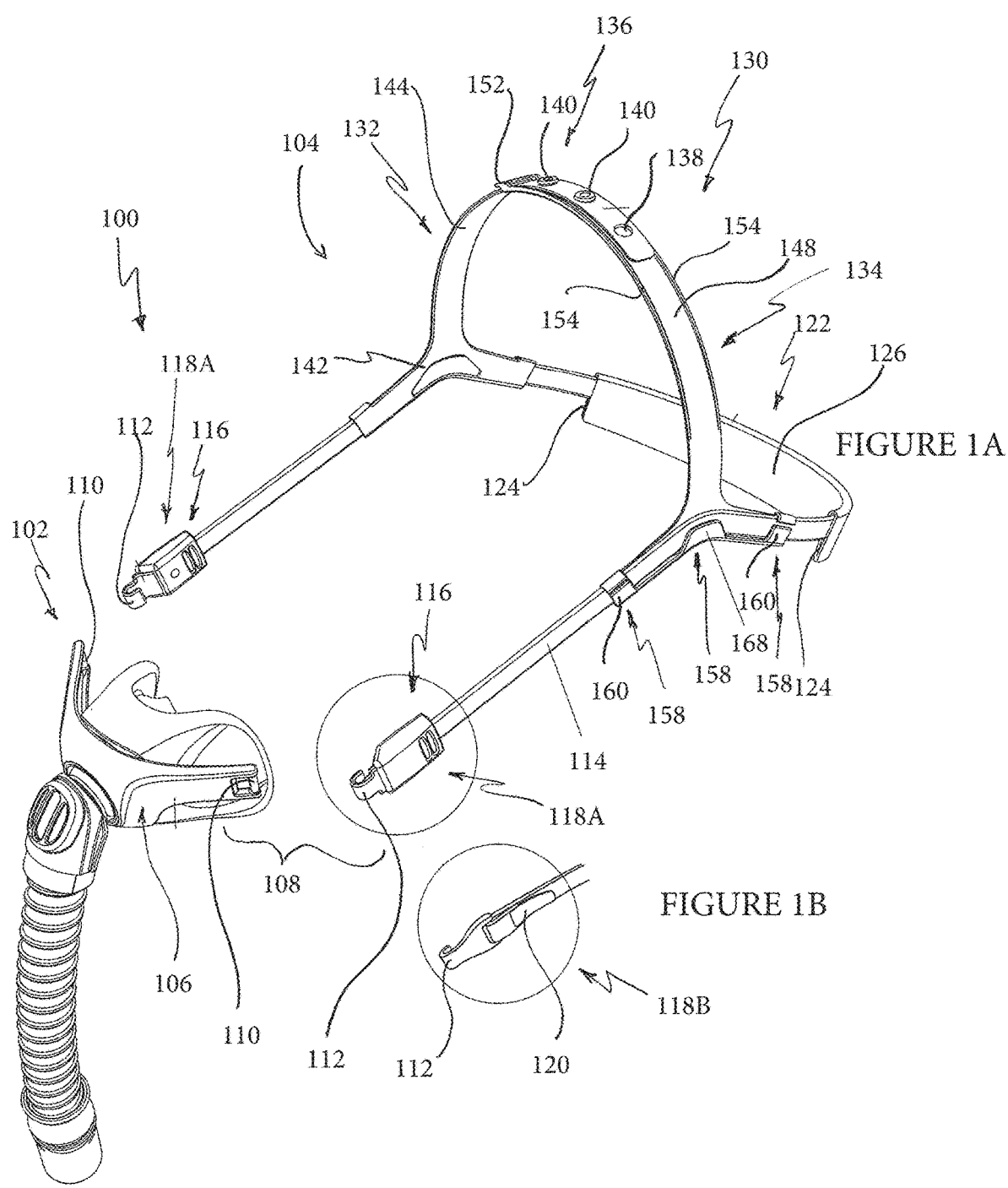
FIGS. 1A and 1B are a partially exploded view of an interface and headgear assembly that is arranged and configured in accordance with certain features, aspects and advantages of the present disclosure.
Figure 2:
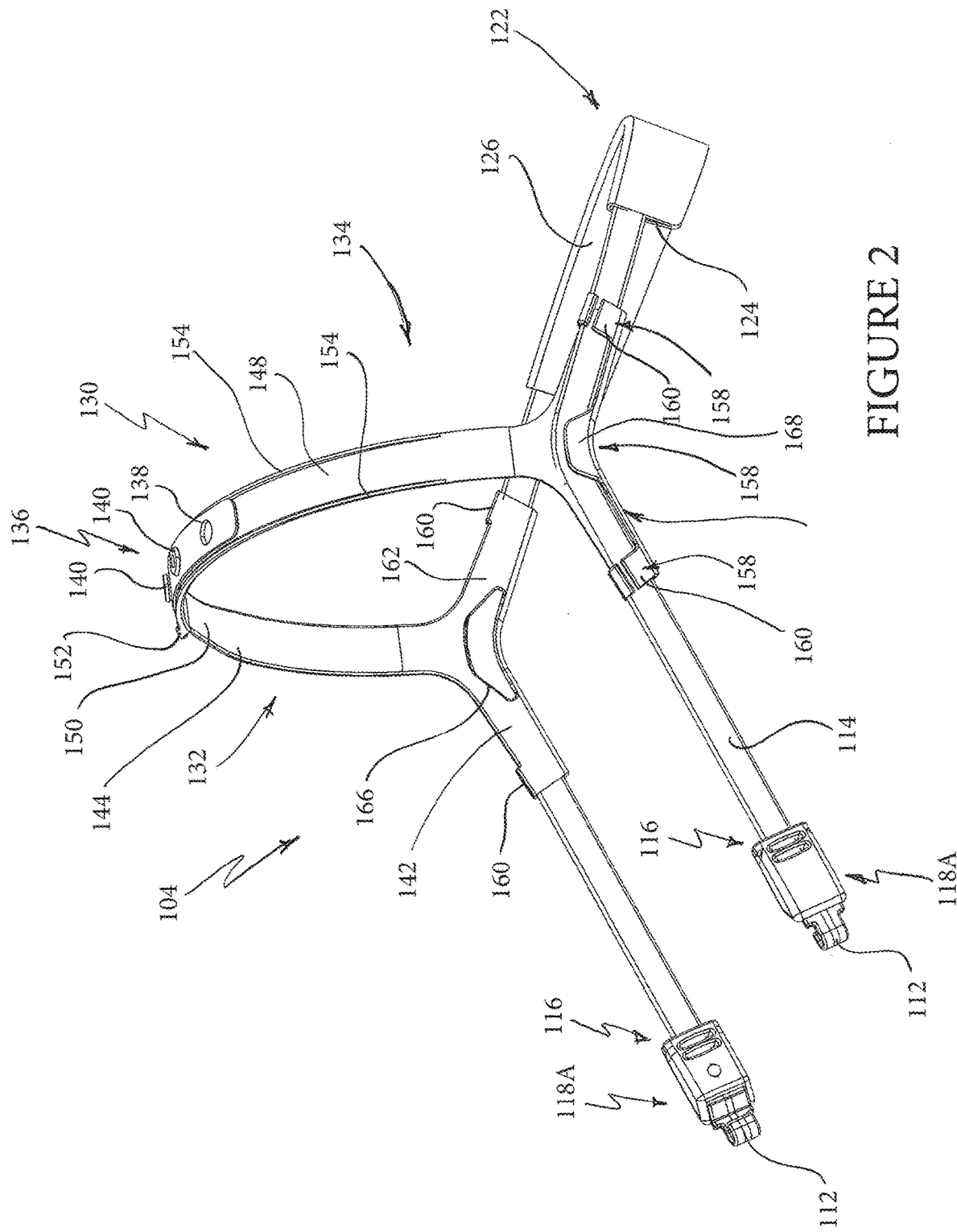
FIG. 2 is a front perspective view of the headgear of FIG. 1A.
Figure 3:
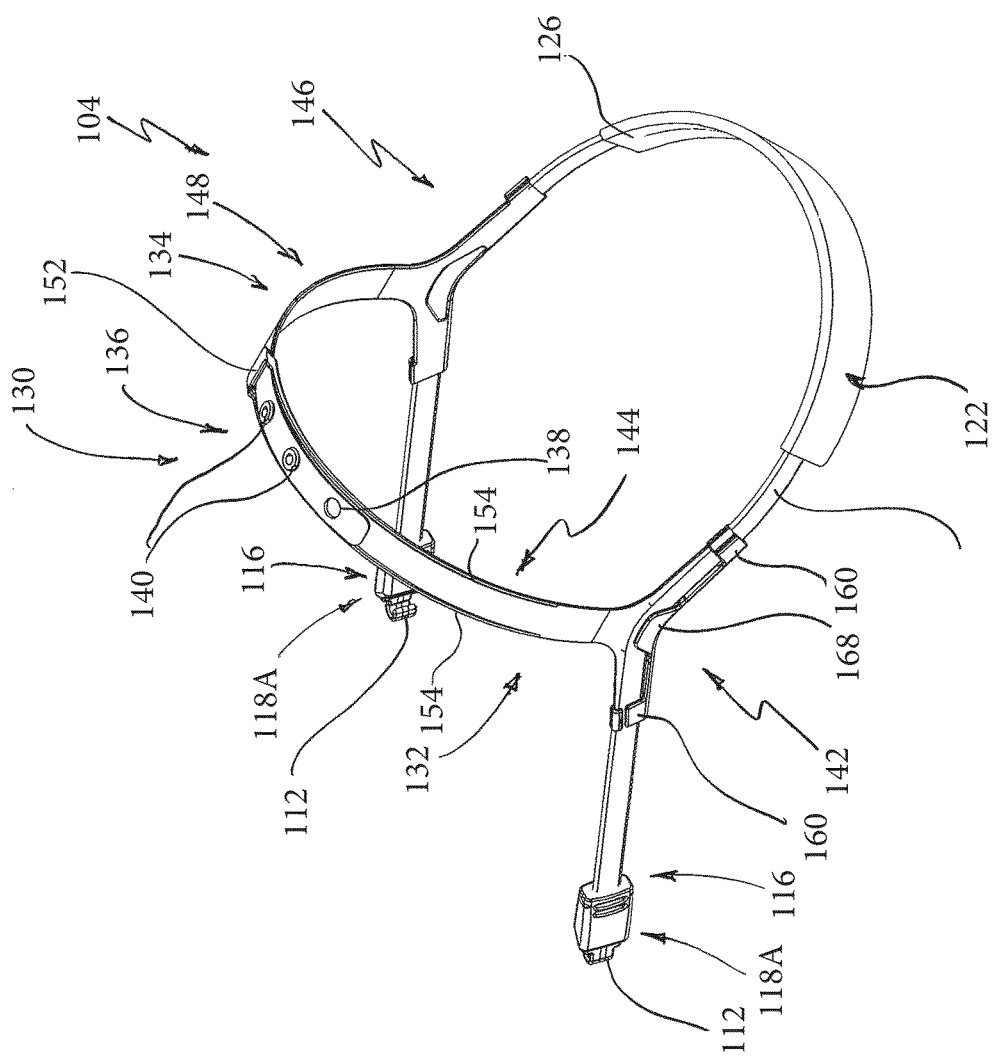
FIG. 3 is a rear perspective view of the headgear of FIG. 1A.
Figure 4:
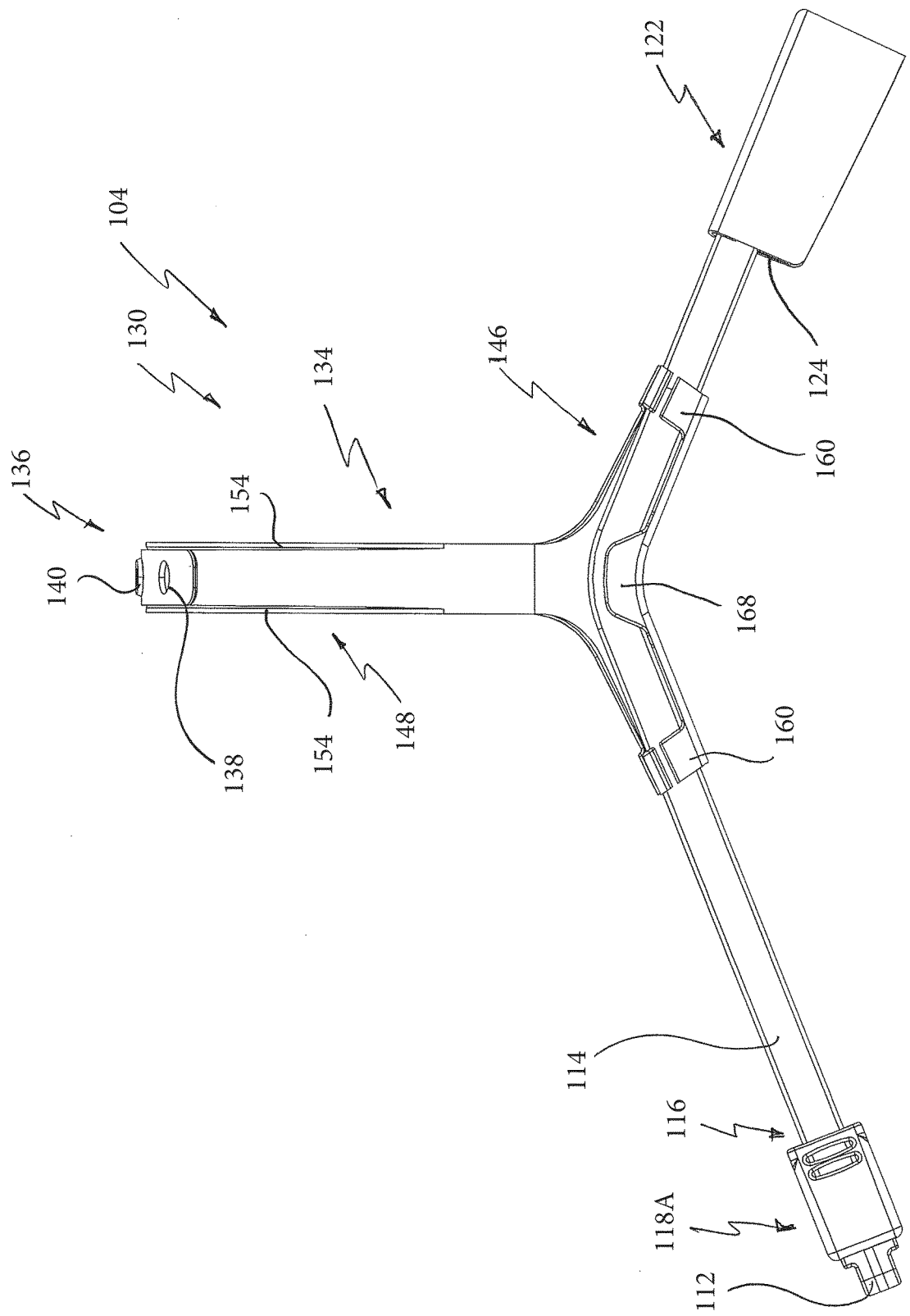
FIG. 4 is a right side view of the headgear of FIG. 1A.
Figure 5:
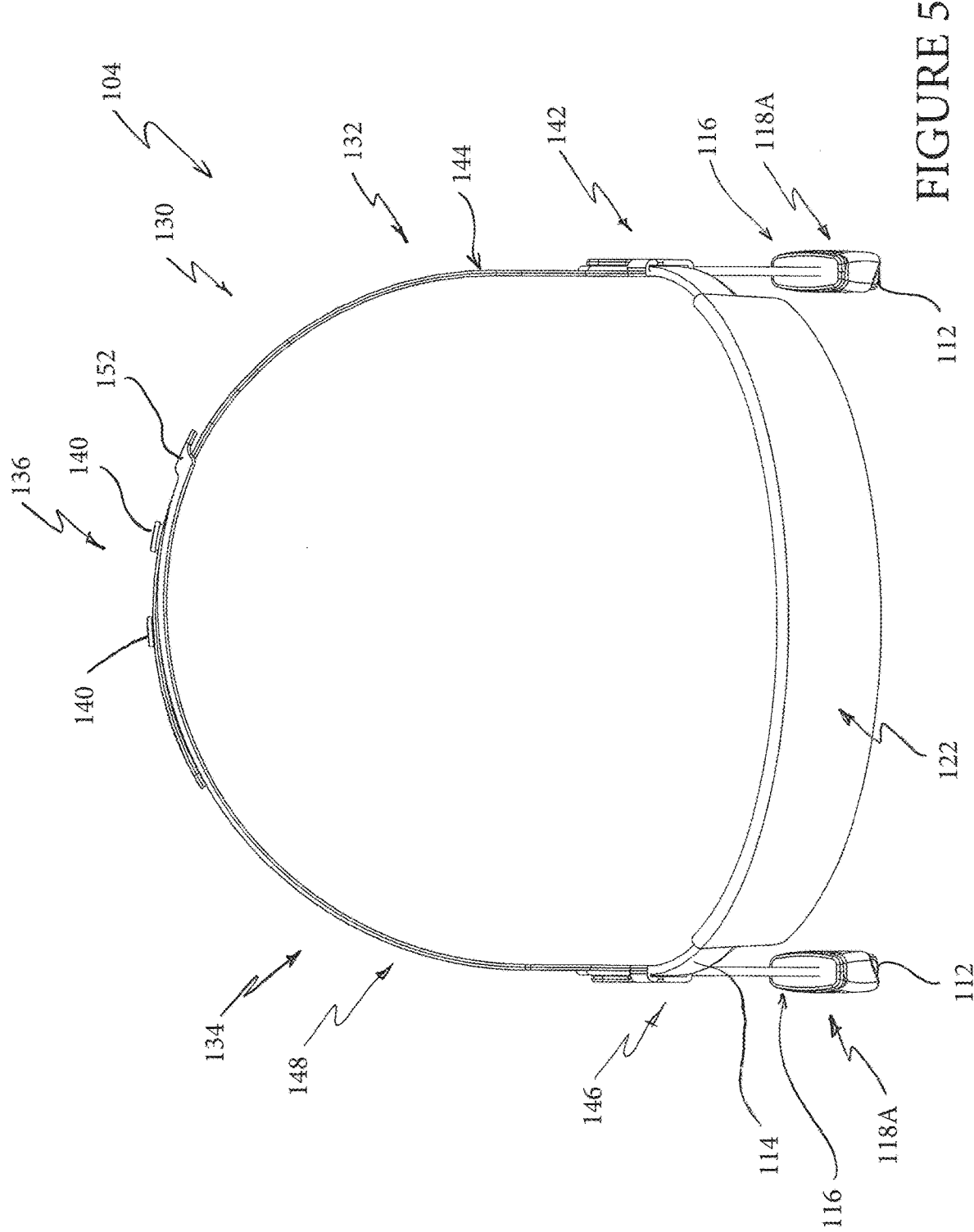
FIG. 5 is a rear view of the headgear of FIG. 1A.

FIGS. 1A and 1B illustrate an interface and headgear assembly 100 that is arranged and configured in accordance with certain features, aspects and advantages of the present disclosure. The assembly 100 features an interface 102 that is removably connectable with a headgear assembly 104.

The patient interface 102 can be any suitable type of patient interface. Examples of suitable types of patient interfaces include face masks, oral masks, nasal masks, nasal pillows masks, nasal cannulae, combinations of oral and nasal masks, tracheal masks, and the like. The illustrated interface 102 is a nasal pillows mask that includes a mask frame 106.

In the illustrated configuration, the mask frame 106 and the headgear assembly 104 can be joined together using any suitable technique. In the illustrated configuration, a post and hook system 108 is used to join the patient interface 102 and the headgear assembly 104. In the illustrated system 108, the mask frame 106 can include a post 110 or the like while the headgear assembly 104 can include a hook 112. The hook 112 can be joined to the post 110 to connect the headgear assembly 104 to the mask frame 106 and the hook 112 can be separated from the post 110 to decouple the headgear assembly 104 from the mask frame 106.

The headgear assembly 104 generally comprises a main strap 114. The main strap 114 can be configured to extend around the back of the head or neck of the wearer. The main strap 114 can have any suitable configuration and can be formed of any suitable material. In some configurations, the main strap 114 can be formed of a stretchable material. In some configurations, the main strap 114 comprises a tubular-knitted elastic strap. In some configurations, the main strap 114 can be of any configuration described in WO2010/131189, published on Nov. 18, 2010, or WO2011/059346, published on May 19, 2011, each of which is hereby incorporated by reference in its entirety. The main strap 114 provides an easy donning of the interface and headgear assembly 100 because the main strap 114 allows the wearer to simply stretch the main strap 114 and fit the interface and headgear assembly 100 to the head.

Figure 17:
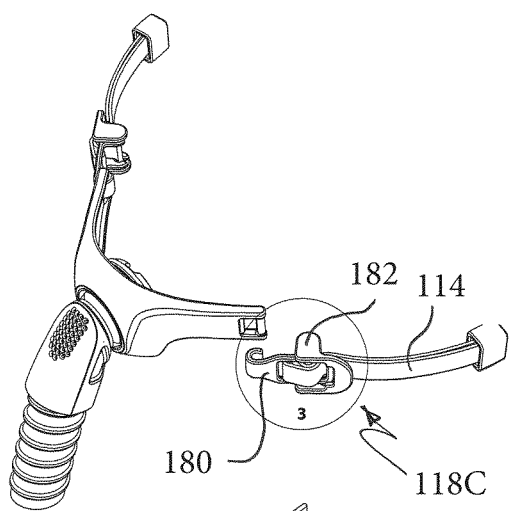
FIG. 17 is a perspective view of a latch adjustment mechanism for adjusting a rear strap.
Figure 18:
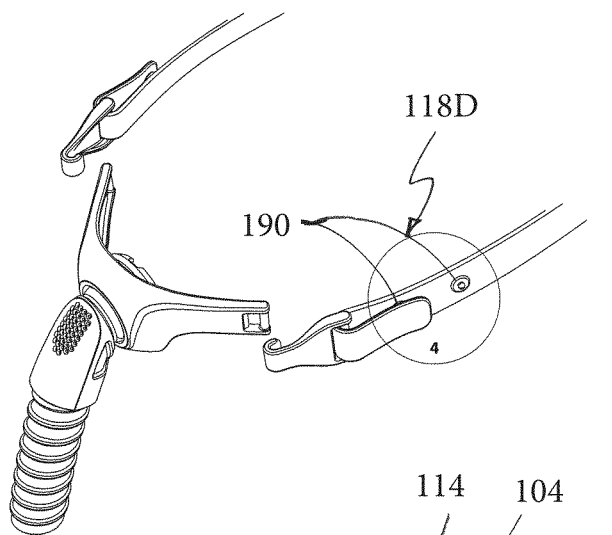
FIG. 18 is a perspective view of a snap adjustment mechanism for adjusting a rear strap.
Figure 19:
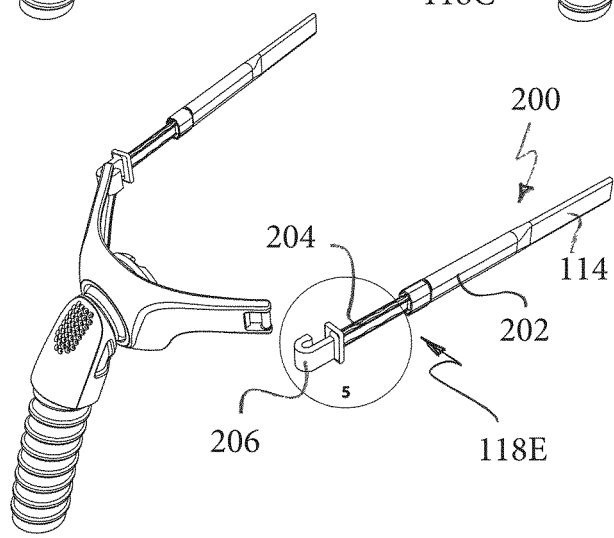
FIG. 19 is a perspective view of a telescoping arm adjustment mechanism for adjusting a rear strap.

In the illustrated configuration, the main strap 114 comprises two ends 116. With continued reference to FIG. 1, each of the two ends 116 can be connected to a corresponding hook 112. Two different types of hook members 118A, 118B are illustrated in FIGS. 1A and 1B. Additional types of hook members 118C, 118D, 118E are illustrated in FIGS. 17-19. Any suitable hook member can be used. The hook members 118A, 118B, 118C, 118D, 118E preferably facilitate easy connection to and disconnection from the interface 102. In some configurations, the hook members 118A, 118B, 118C, 118D, 118E support smooth rotation during fitting or connection. In other words, the hook members 118A, 118B, 118C, 118D, 118E can rotate into position relative to the posts 110.

One of the hook members 118A is designed to create a fixed length to the main strap 114. In other words, a position of the first of the two hook members 118A on or relative to the main strap 114 is not adjustable. The hook member 118A can capture at least a portion of the main strap 114 or can be secured to the main strap 114 in any other suitable manner. In some configurations, the hook members 118A is an assembly that is overmoulded into position onto the main strap 114.

The second of hook members 118B is adjustable relative to the main strap 114 and allows the length of the main strap 114 to be adjusted. In the illustrated configuration, the hook member 118B includes an opening through which the end 116 of the main strap 114 can be threaded before being doubled back and secured to itself. In the illustrated configuration, a hook and loop fastener 120 can be used. The hook and loop fastener 120 can include a hook tab that is secured to the main strap 114. In some configurations, the hook tab can be ultrasonically welded, or RF welded, to a nylon, polyester or similar covered substrate, which can form a portion of the main strap 114. In some configurations, the hook portion of the hook and loop fastener 120 can be positioned on the end of the strap 114 with the loop portion being positioned on the portion of the strap between the two ends of the strap 114.

With reference to FIG. 17, the third of the hook members 118C is designed to be adjustable and allows the length of the main strap 114 to be adjusted. The main strap 114 feeds through a first latch component 180 and a second latch component 182. The first latch component 180 and the second latch component can be pivotally connected, for example but without limitation. The position of the hook member 118C along the main strap 114 can be adjusted until the first latch component 180 and the second latch component 182 are pivoted to a locked position. When in the locked position, the hook member 118C is secured in position along the main strap 114. When in the unlocked position, the hook member 118C can be adjusted along the main strap 114 such that the length of the main strap 114 can be increased and decreased.

With reference to FIG. 18, the fourth of the hook members 118D also is designed to be adjustable and allows the length of the main strap 114 to be adjusted among a plurality of predetermined lengths. In the illustrated configuration, the main strap 114 includes a plurality of snaps 190. The snaps 190 away from the end of the main strap 114 cooperate with a portion that is positioned on the end of the main strap 114. As such, the portion that is positioned on the end of the main strap 114 can be moved among the plurality of the snaps 190 to allow for adjustment. In some configurations, the main strap 114 can be provided with two or three different set points (e.g., to correspond to large, medium and small sizes). Other configurations also are possible keeping in mind the goal of providing for simple, yet effective, adjustability.

With reference to FIG. 19, the fifth of the hook members 118E is adjustable and allows the length of the main strap 114 to be adjusted through a telescoping mechanism 200. The telescoping mechanism 200 generally comprises an outer sleeve member 202 and an inner arm 204. In the illustrated configuration, the outer sleeve member 202 is secured to the strap 114 while the inner arm 204 is secured to a hook element 206. In some configurations, the orientation is switched. The outer sleeve member 202 can define an inner passage. The inner passage can include one or more ridges. The inner arm 204 can include one or more recesses. In some configurations, the outer sleeve member can have recesses on the inner passage while the inner arm includes ridges. Other configurations also are possible. By squeezing the outer sleeve member 202, the inner arm 204 can translate relative to the outer sleeve member 202. In some configurations, the outer sleeve 202 is squeezed in a direction that is generally normal or perpendicular to the interlocking recesses and ridges such that squeezing the outer sleeve 202 results in movement of a portion of the outer sleeve 202 away from the inner arm 204. Accordingly, the illustrated configuration provides adjustability. The adjustability provides a plurality of set points depending upon the distance between the ridges and the recesses. Other detent arrangements, locks and retention arrangements can also be used.

Figure 23:
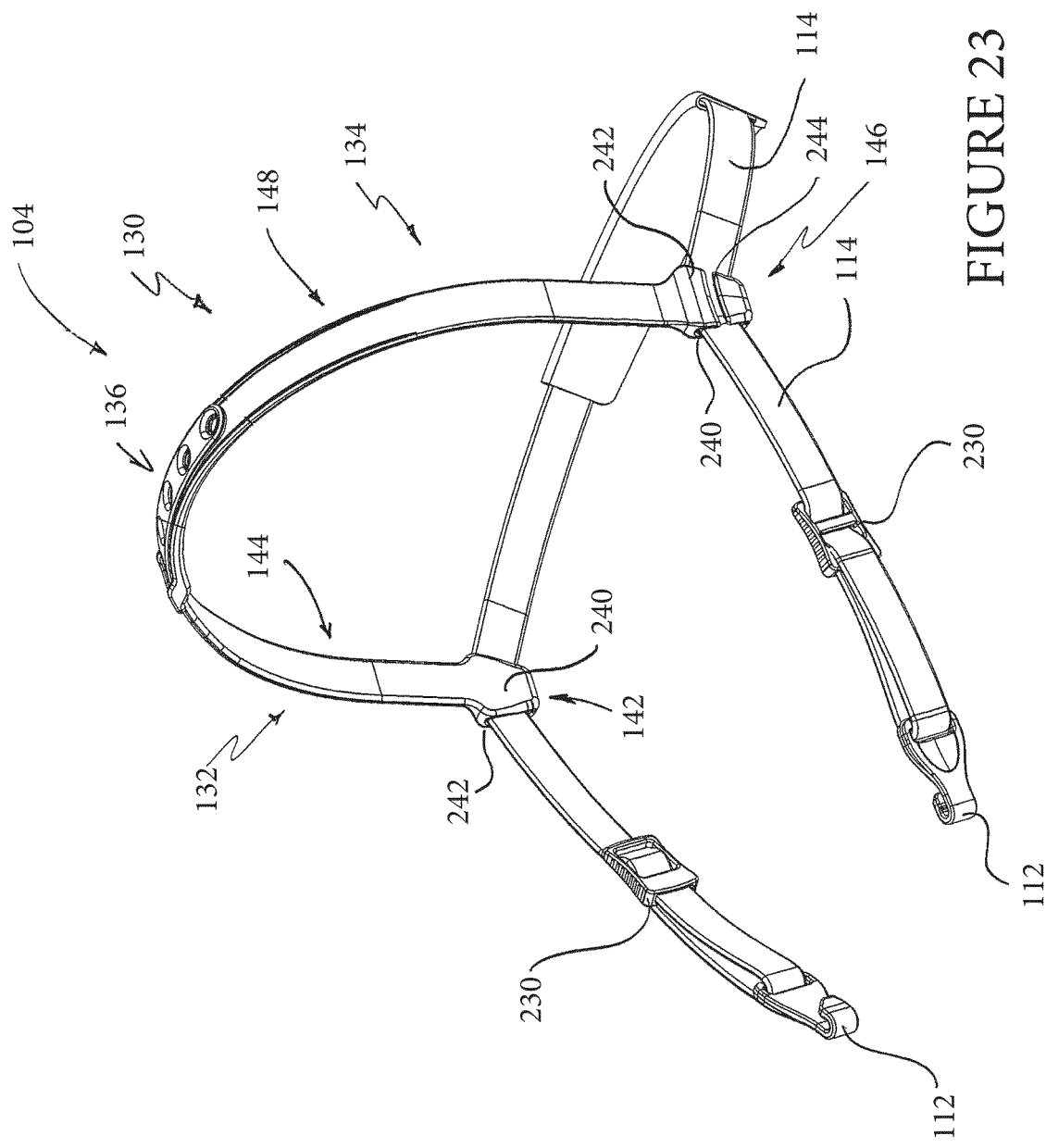
FIG. 23 is a perspective view of a headgear assembly.
Figure 24:
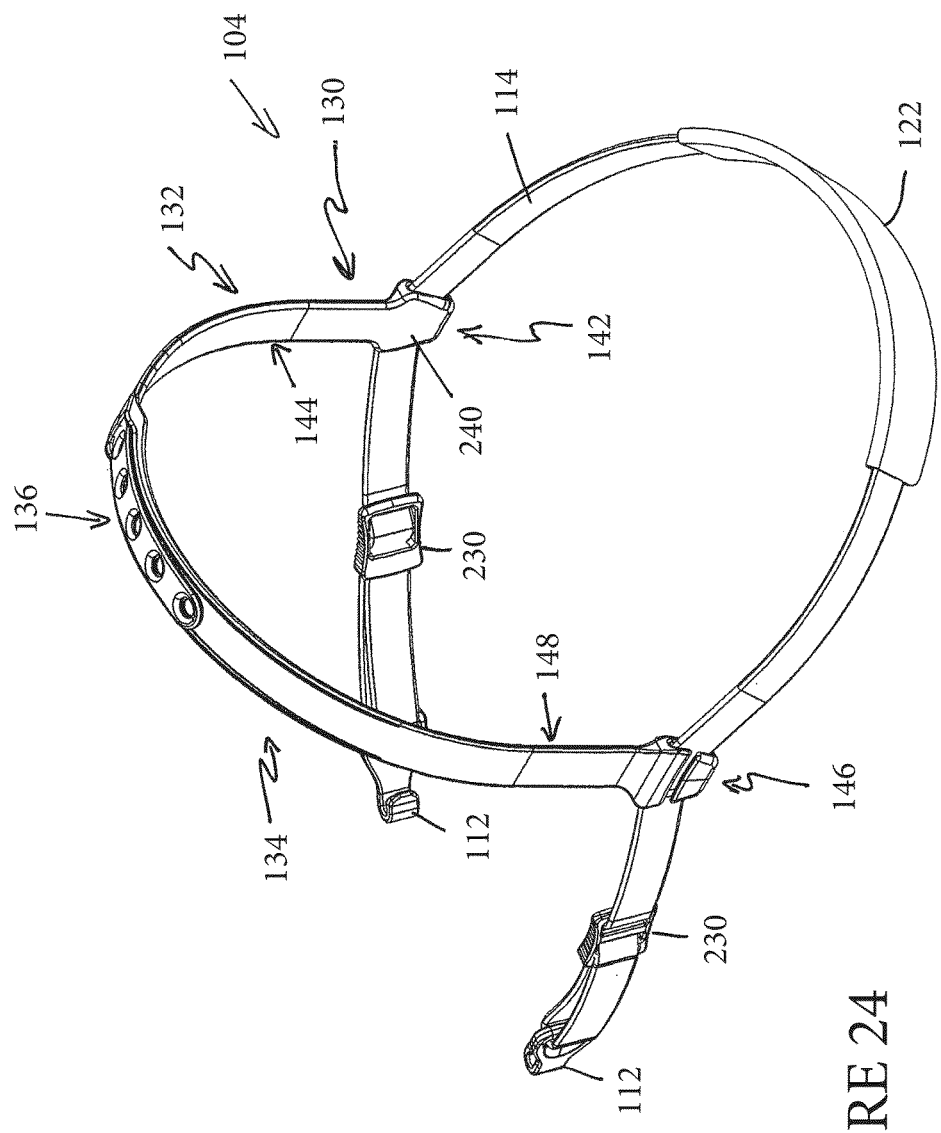
FIG. 24 is another perspective view of the headgear assembly of FIG. 23.
Figure 25:
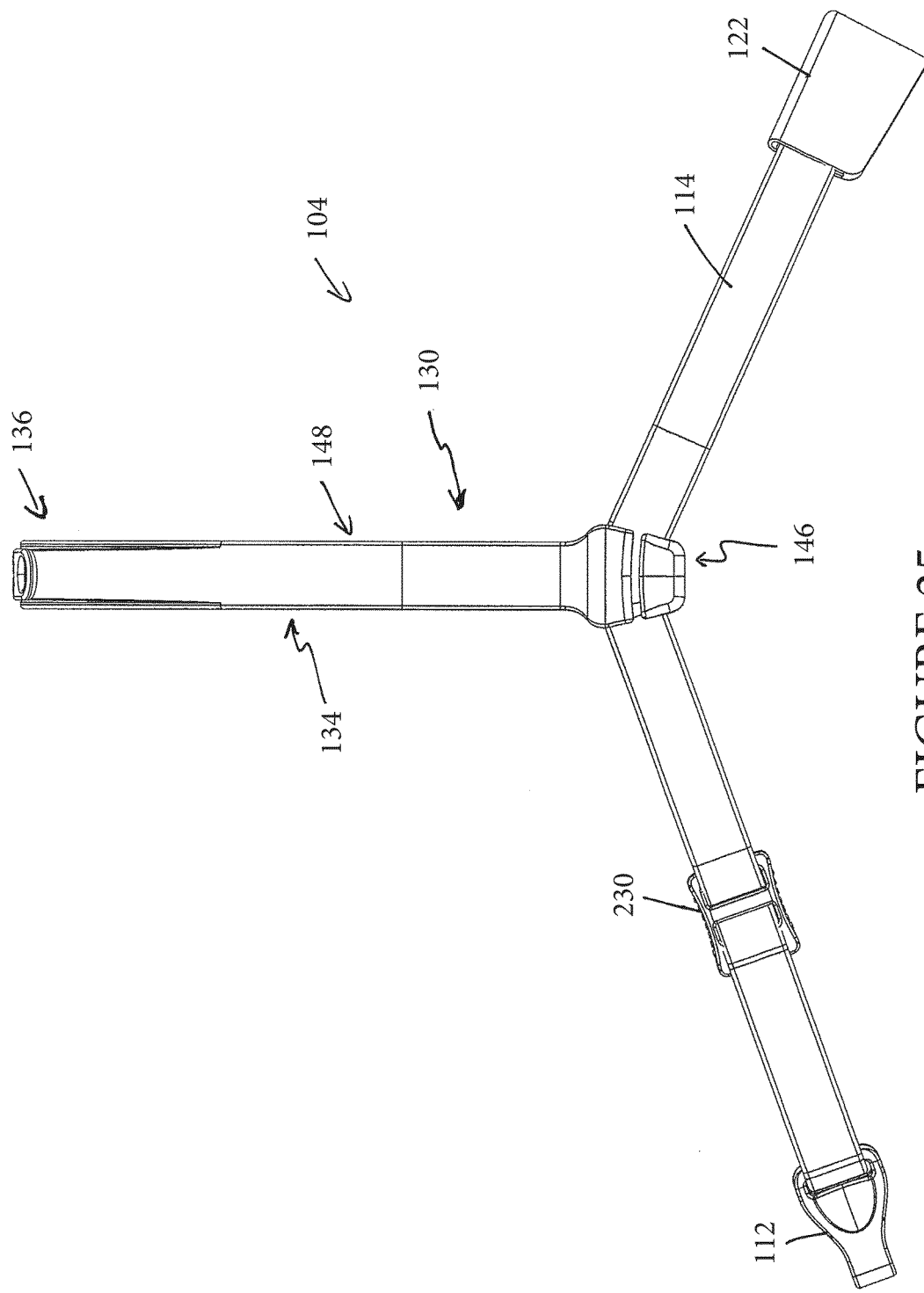
FIG. 25 is a side elevation view of the headgear assembly of FIG. 23.
Figure 26:
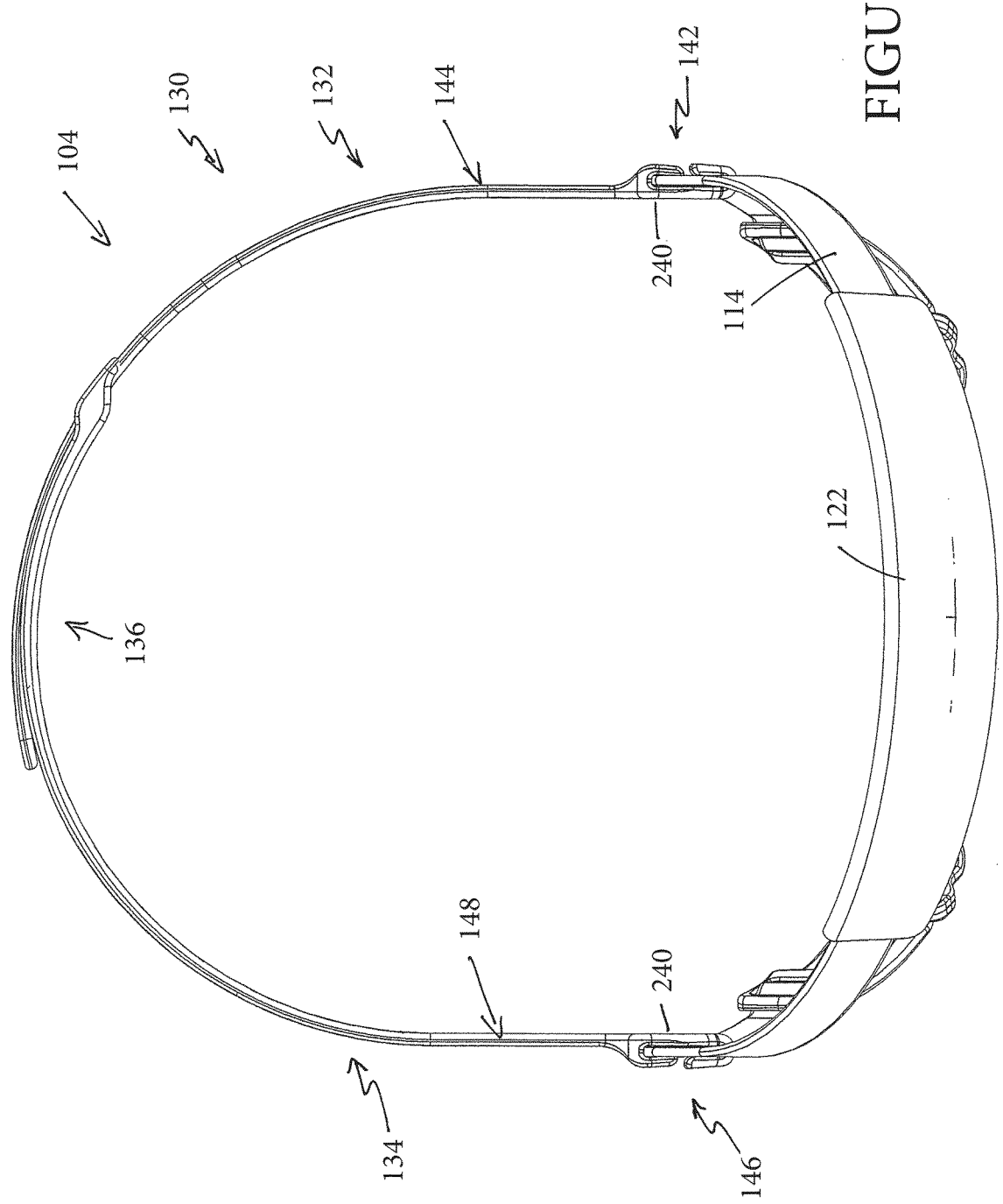
FIG. 26 is a rear elevation view of the headgear assembly of FIG. 23.
Figure 27:
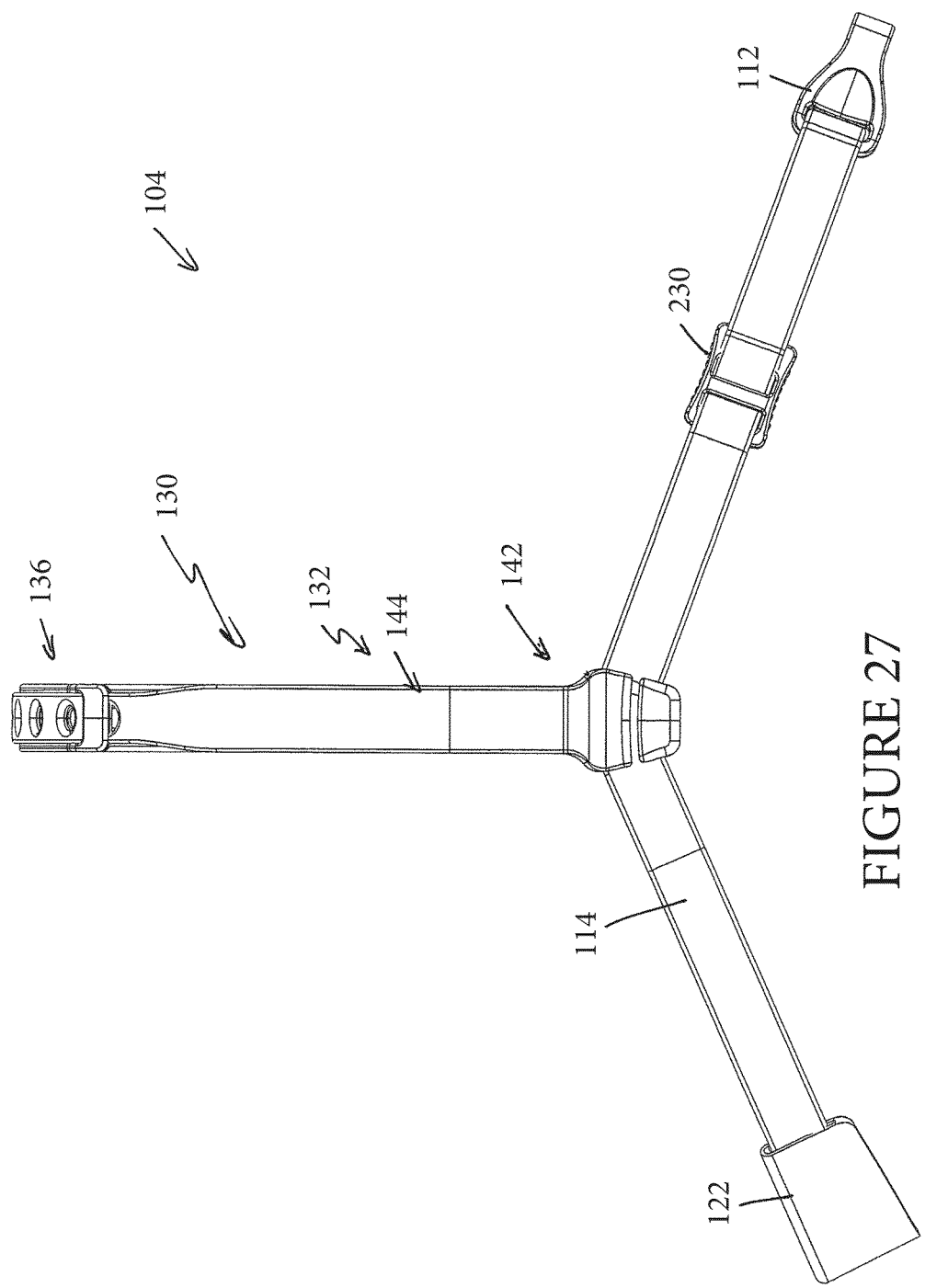
FIG. 27 is a side elevation view of the headgear assembly of FIG. 23.
Figure 28:
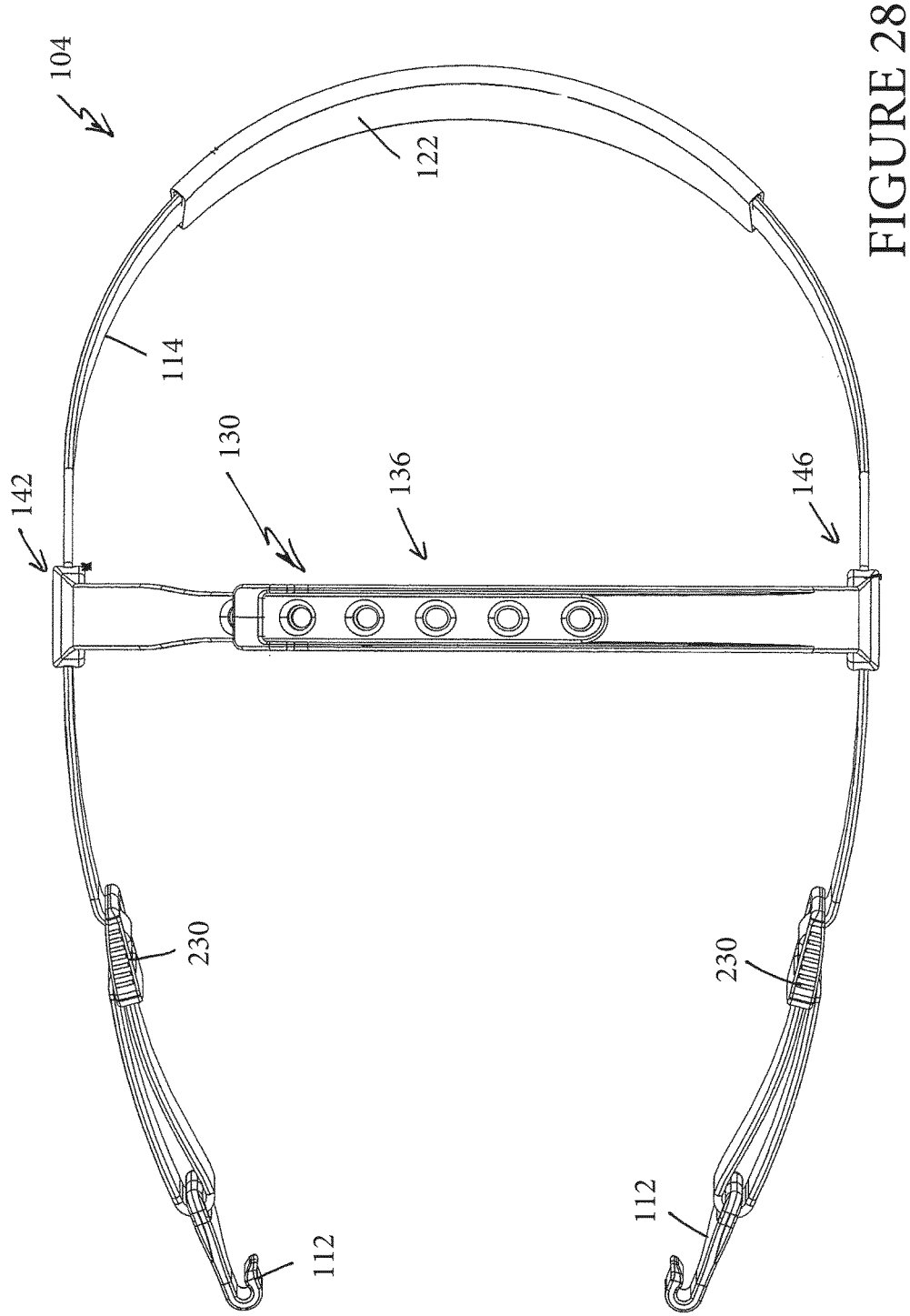
FIG. 28 is a top view of the headgear assembly of FIG. 23.
Figure 29:
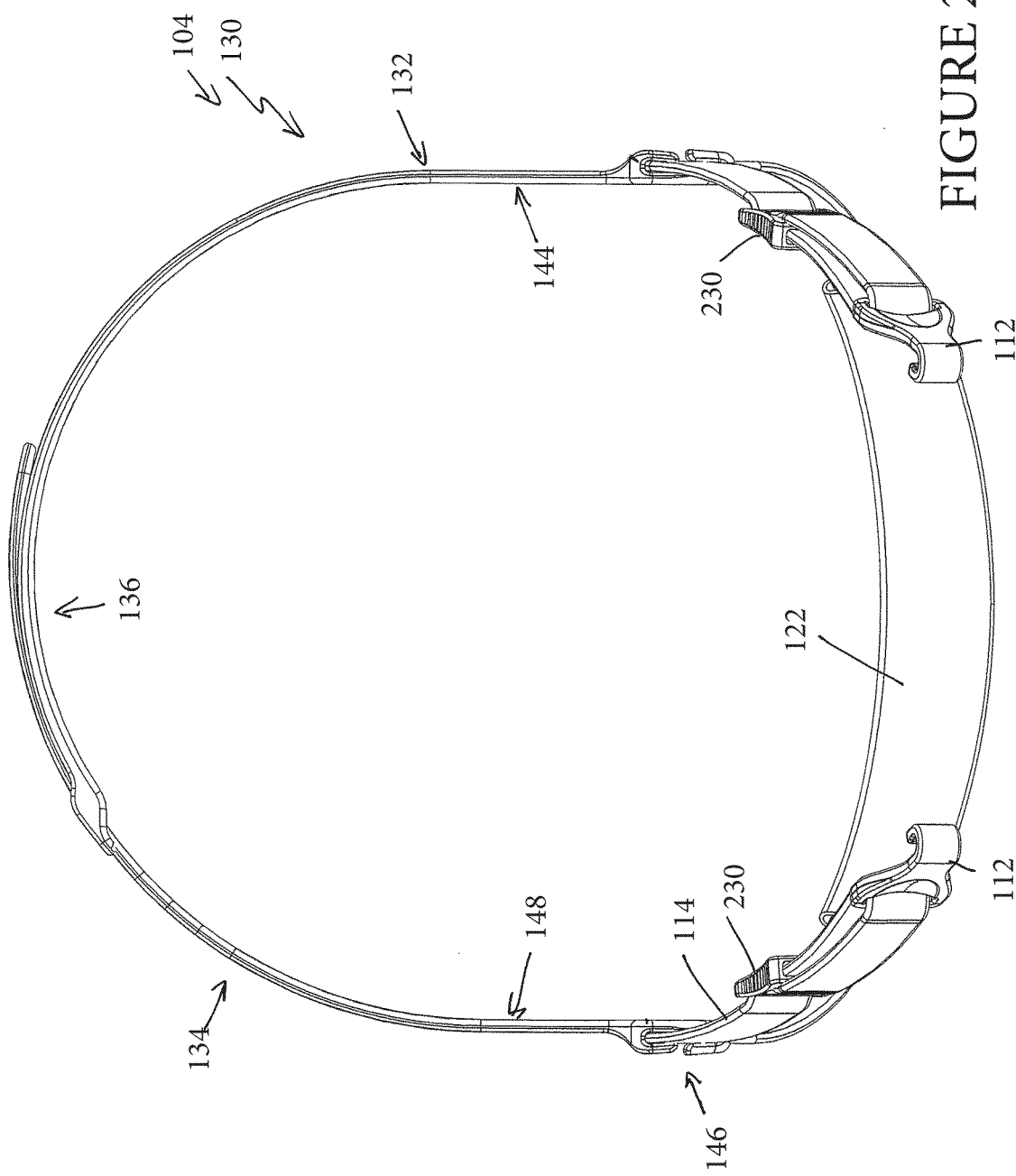
FIG. 29 is a front elevation view of the headgear assembly of FIG. 23.
Figure 30:
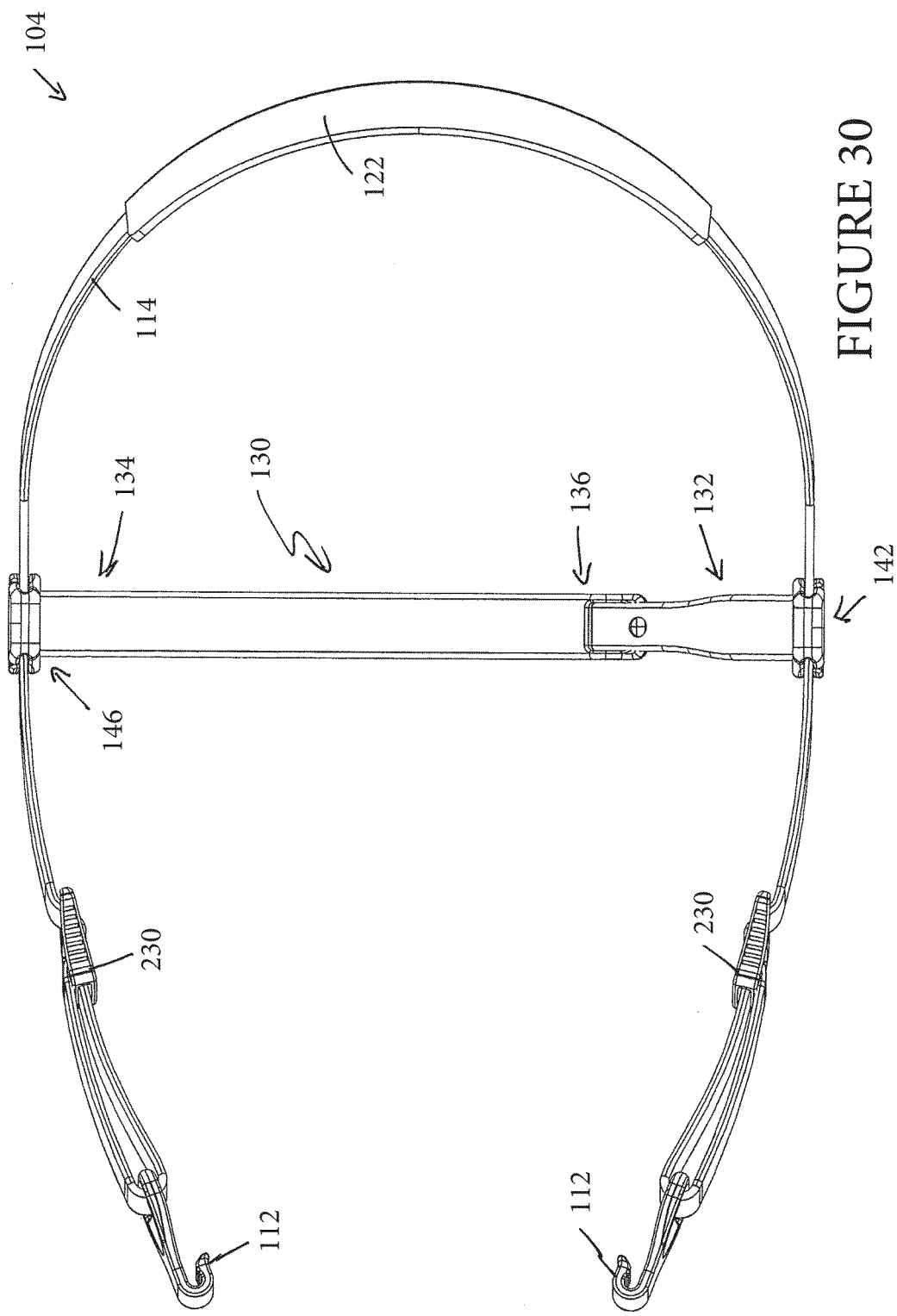
FIG. 30 is a bottom view of the headgear assembly of FIG. 23.
Figure 31:
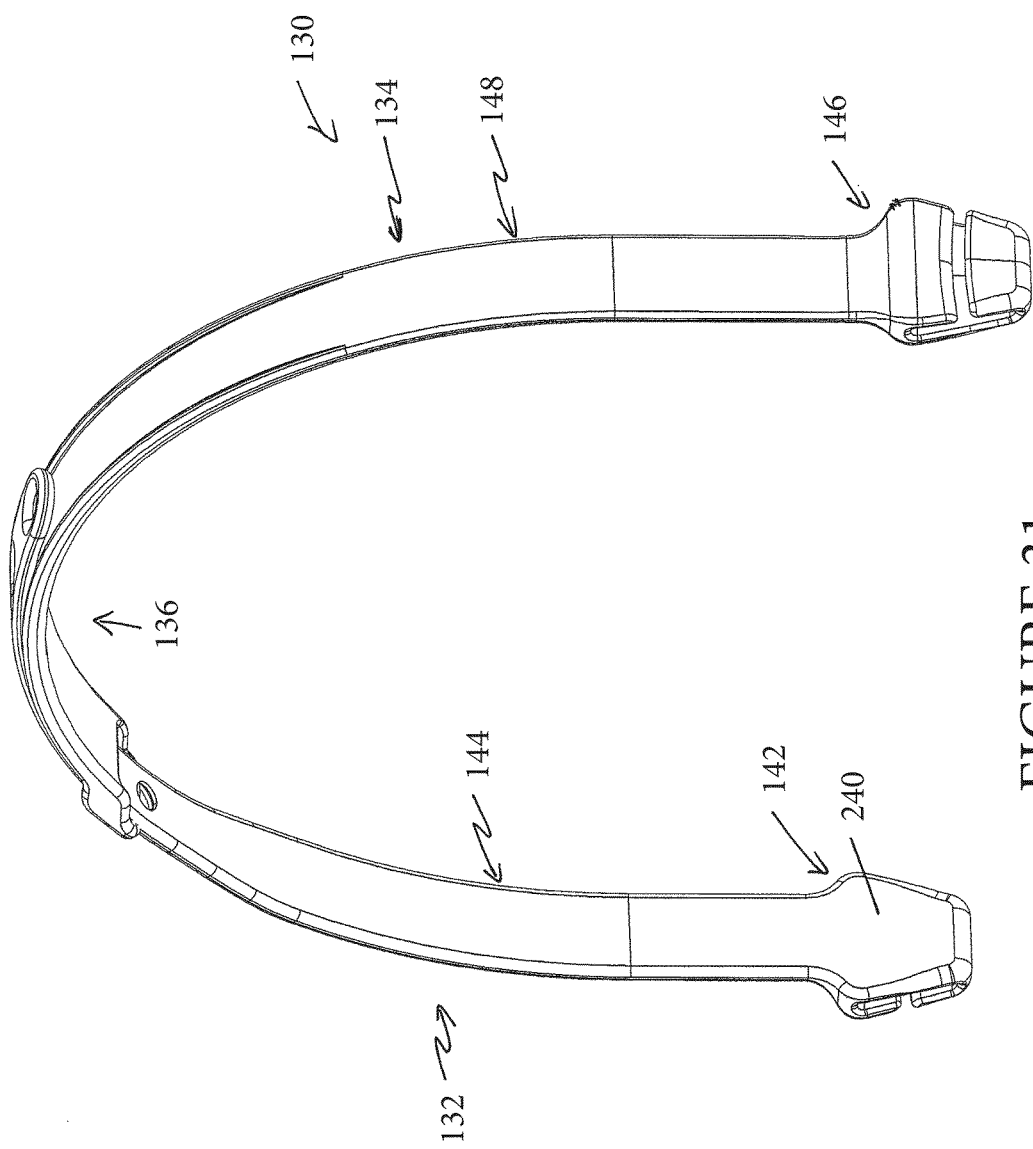
FIG. 31 is a perspective view of a crown strap assembly of the headgear assembly of FIG. 23.
Figure 32:
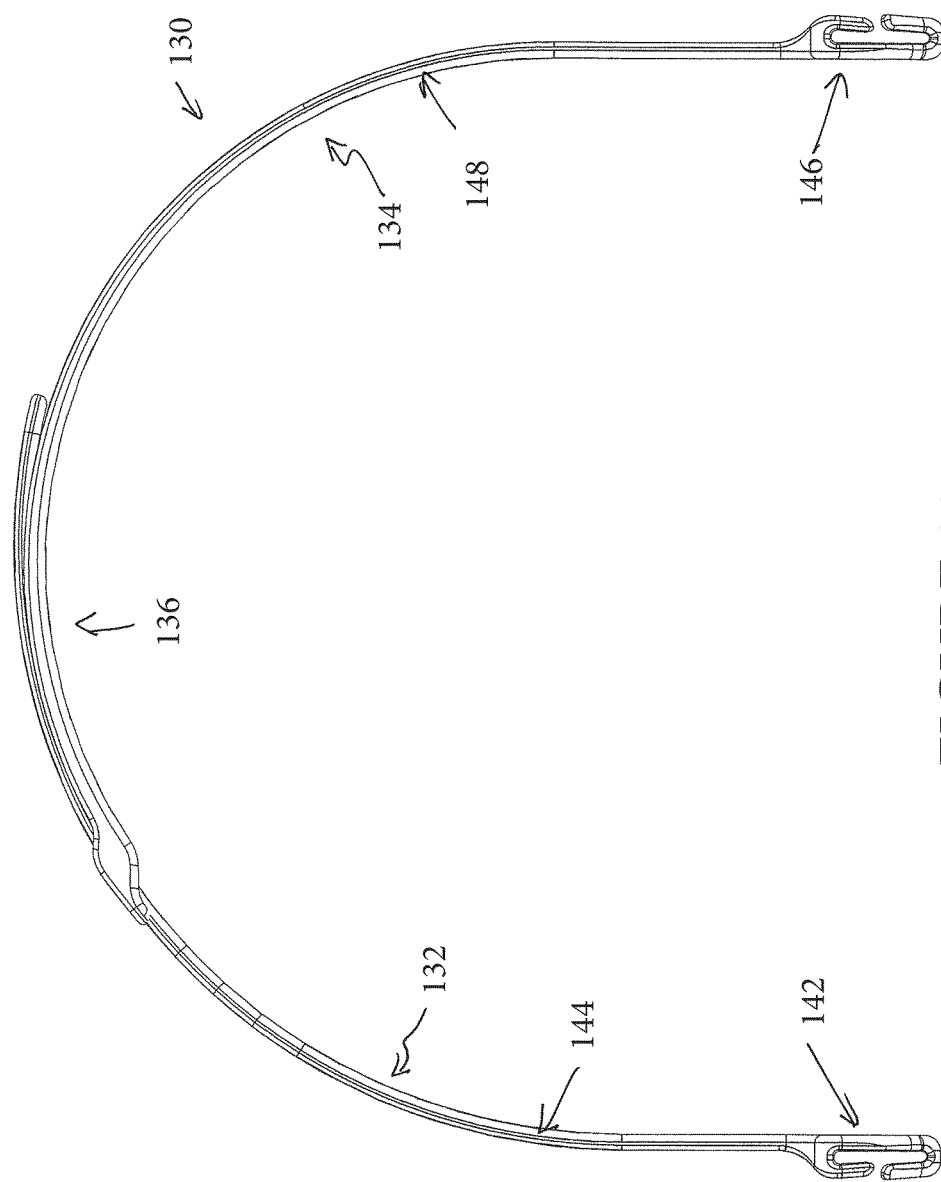
FIG. 32 is a front view of the crown strap assembly of FIG. 31.

In some configurations, such as that illustrated in FIG. 23, the adjustability can be provided through the use of buckles 230 or the like. The strap 114 can be threaded through the hooks 112 and secured to a desired length by threading through the buckles 230. Other suitable configurations also can be used keeping in mind a desire to provide adjustability to the length of the strap 114.

As shown in FIG. 15, in some configurations, the main strap 114 can be used without any further components. In other words, the main strap 114 can be secured to the interface 102 and provide a retention force to maintain the interface 102 in position for use. In such configurations, the main strap 114 may also comprise the hook members 118A (or the hook members 118B).

With reference to FIG. 14, to enhance comfort, a sleeve 122 can be positioned along the main strap 114 between the ends 116. The sleeve 122 can be configured in any suitable manner and the sleeve can be formed of any suitable material. In some configurations, the sleeve 122 is repositionable along the main strap 114 in any location between the ends 116. In some configurations, the sleeve 122 is secured to the main strap 114 and cannot be removed and/or cannot be moved along the length of the main strap 114.

The sleeve 122 can be formed of polyester, nylon, micro fibre, fleece, or any other suitable materials, including those that are quick drying and/or moisture wicking. In some configurations, the sleeve 122 forms a flattened tube-like structure that defines an elongate passage that terminates at openings 124. In configurations in which the sleeve 122 is removable, the openings 124 can be sufficiently large or flexible to accommodate the hook members 118A, 118B. In configurations using the removable hook members 118B, however, the openings 124 need not be sufficiently large or flexible to accommodate the hook members 118B. The main strap 114 can be inserted into one of the openings 124 and passed through the passage.

The illustrated sleeve 122 also has a contact surface 126. The contact surface 126 is the surface that will be directly in contact with the wearer. In the illustrated configuration, the contact surface 126 is enlarged relative to the corresponding surface of the main strap 114. In the illustrated configuration, the contact surface 126 and the opposite surface both can provide an elongate flattened surface. By providing an elongate flattened surface, labeling can be positioned on the sleeve 122, which can be used to provide guidance for the proper orientation of the main strap 114 when donning the interface and headgear assembly 100. In some configurations, the contact surface 126 can be provided with surface texturing or the like to enhance gripping on short haired or bald headed patients.

With reference again to FIG. 1, the headgear assembly 104 also can comprise a crown strap assembly 130. In some configurations, the crown strap assembly 130 can be selectively coupled to and decoupled from the main strap 114. By including a detachable crown strap assembly 130, the headgear assembly 104 can provide more options to the user, which can enhance the individualized comfort and/or support sought by users. In addition, using the crown strap assembly 130 can improve stability of the headgear assembly 104. Moreover, because the crown strap assembly 130 is designed to pass over the top of the head of the user, using the crown strap assembly 130 can reduce slippage of the main strap 114 during use.

Turning now to FIGS. 10-13, the crown strap assembly 130 is shown separated from the main strap 114. In the illustrated configuration, the crown strap assembly 130 is adjustable. Accordingly, the illustrated crown strap assembly 130 comprises a first portion 132 and a second portion 134. The first portion 132 and the second portion 134 can be adjustably connected. In the illustrated configuration, an adjustment mechanism 136 couples the first portion 132 and the second portion 134. The first portion 132 connects to the main strap 114 and the second portion 134 while the second portion 134 connects to the main strap 114 and the first portion 132. In other words, the first portion 132 and the second portion 134 are connected to the main strap 114 and to each other. In other configurations, the crown strap 130 is not adjustable and can be constructed as a single piece.

The adjustment mechanism 136 in the configuration illustrated in FIG. 1A comprises a plurality of apertures 138 and one or more posts 140. In some configurations, two posts 140 are provided and three apertures 138 are provided. The illustrated configuration provides at least three different settings such that the adjustment mechanism 136 provides three different length or height settings for the crown strap assembly 130. That is, a change in length of the crown strap 130 changes a height of ends of the crown strap 130 on a user's head in use. Other types of adjustment mechanisms and other numbers of settings can be used.

The posts 140 can comprise a stem and a head portion. The head portion of the posts 140 can be very closely sized or slightly oversized relative to the aperture 138. The apertures 138 can snap fit over the head portions of the posts 140. In such a manner, a secure coupling can be provided.

Figure 21:
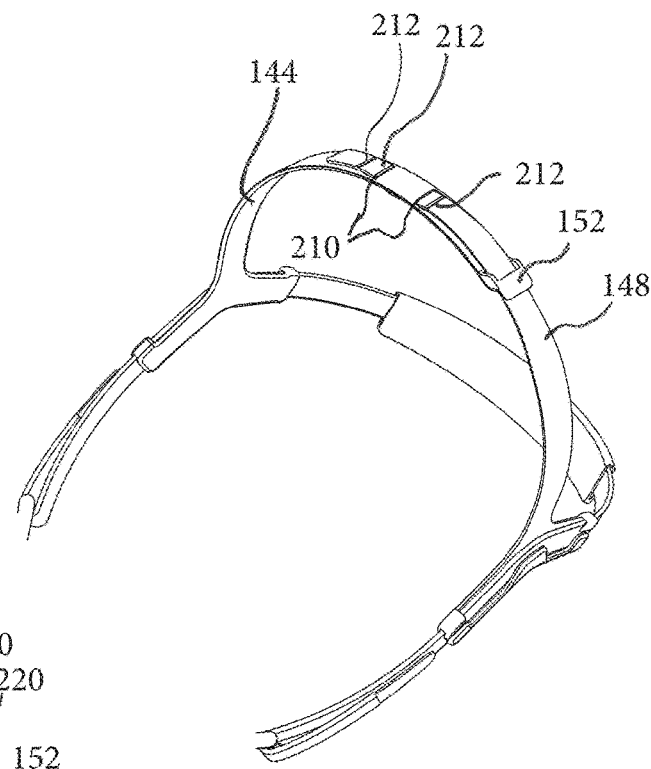
FIG. 21 is a perspective view of a crown strap adjustment configuration.

Other manners of securing the first portion 132 and the second portion 134 together also can be used. For example, as shown in FIG. 21, the adjustment mechanism 136 can include two or more slots 210 and a plurality of transverse ridges 212. In the illustrated configuration, the first portion 132 comprises two parallel slots 210. The slots 210 do not extend the full width of the first portion 132. By being generally parallel, the slots 210 can interact with the ridges 212 of the second portion 134. In some configurations, however, the slots 210 may not be generally parallel. The ridges 212 can extend the full width or at least some portion of the width of the second portion 134. By spacing the ridges 212 at desired increments, a plurality of discrete and predetermined sizes can be defined for the crown strap assembly 130.

Figure 22:
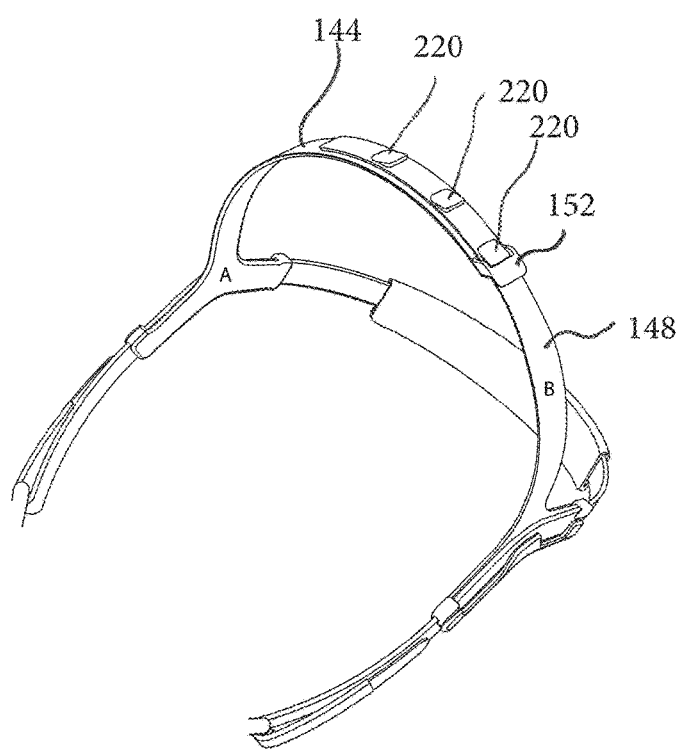
FIG. 22 is a perspective view of another crown strap adjustment configuration.

With reference to FIG. 22, another adjustment mechanism 136 is illustrated. In the illustrated configuration, the first portion 132 can include one or more wedges or flaps 220 while the second portion 134 can include corresponding slots 222. In some configurations, the same number of wedges/flaps 220 and slots 222 can be used (e.g., 3 wedges/flaps 220 and 3 slots 222). In some configurations, fewer wedges/flaps 220 than slots 222 can be provided. In some configurations, more wedges/flaps 220 than slots 222 can be provided. The illustrated configuration provides for adjustability between discrete and predetermined sizes for the crown strap assembly 130. In some configurations, three or four sizes can be provided.

Figure 34:
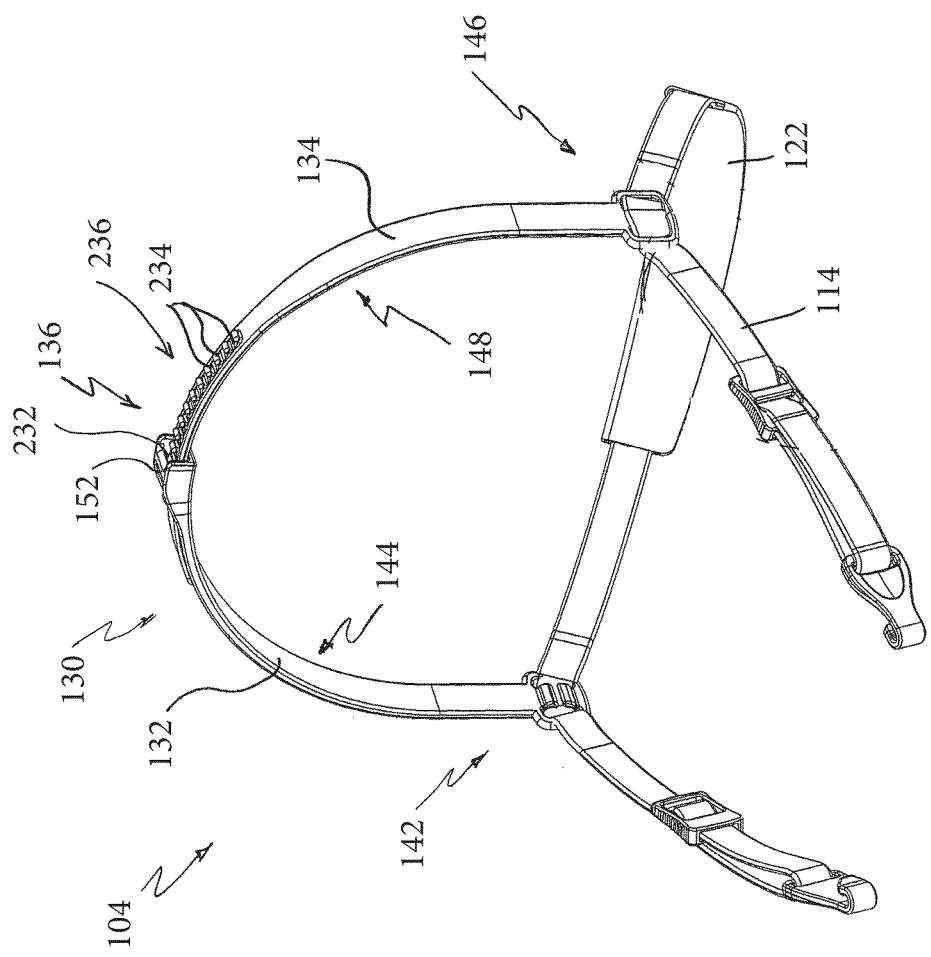
FIG. 34 is a perspective view of a headgear assembly.
Figure 35:
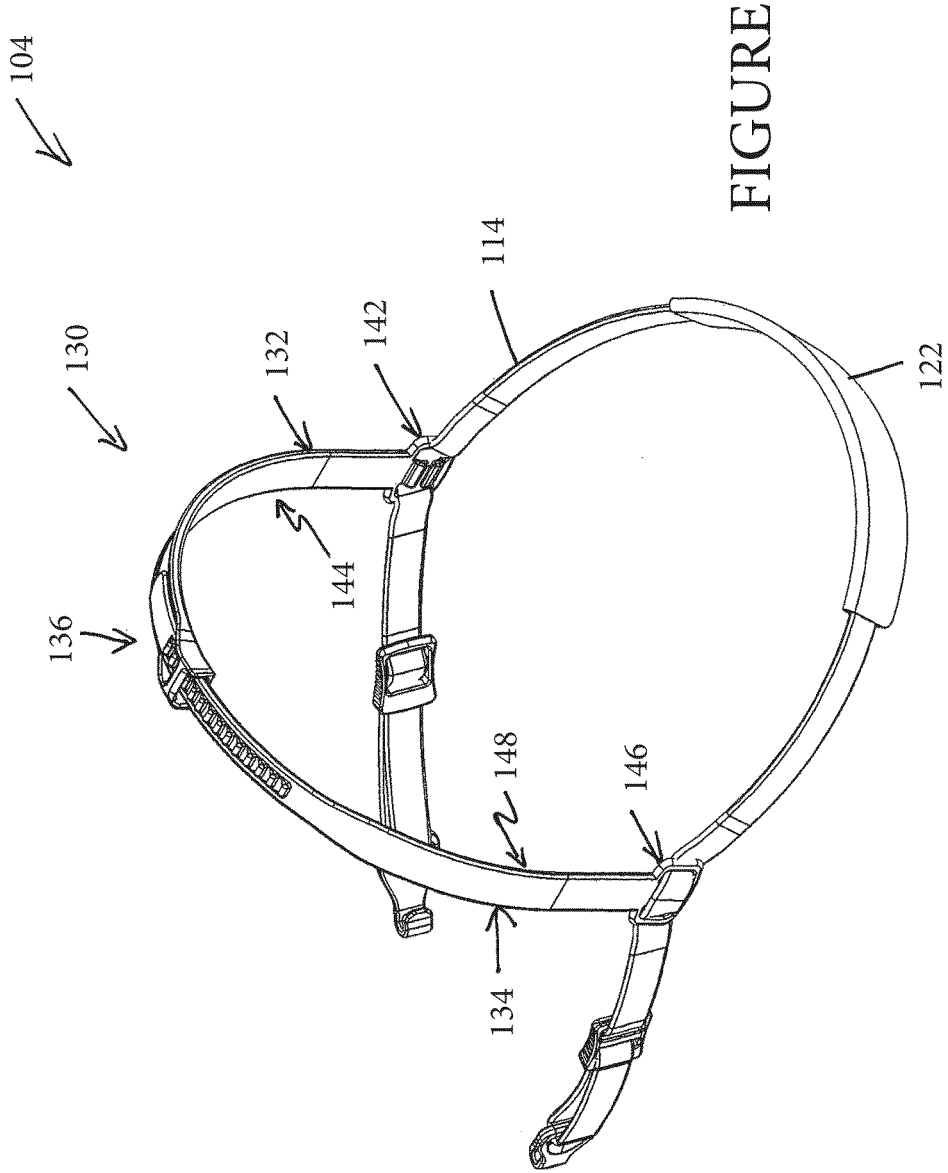
FIG. 35 is another perspective view of the headgear assembly of FIG. 34.
Figure 36:
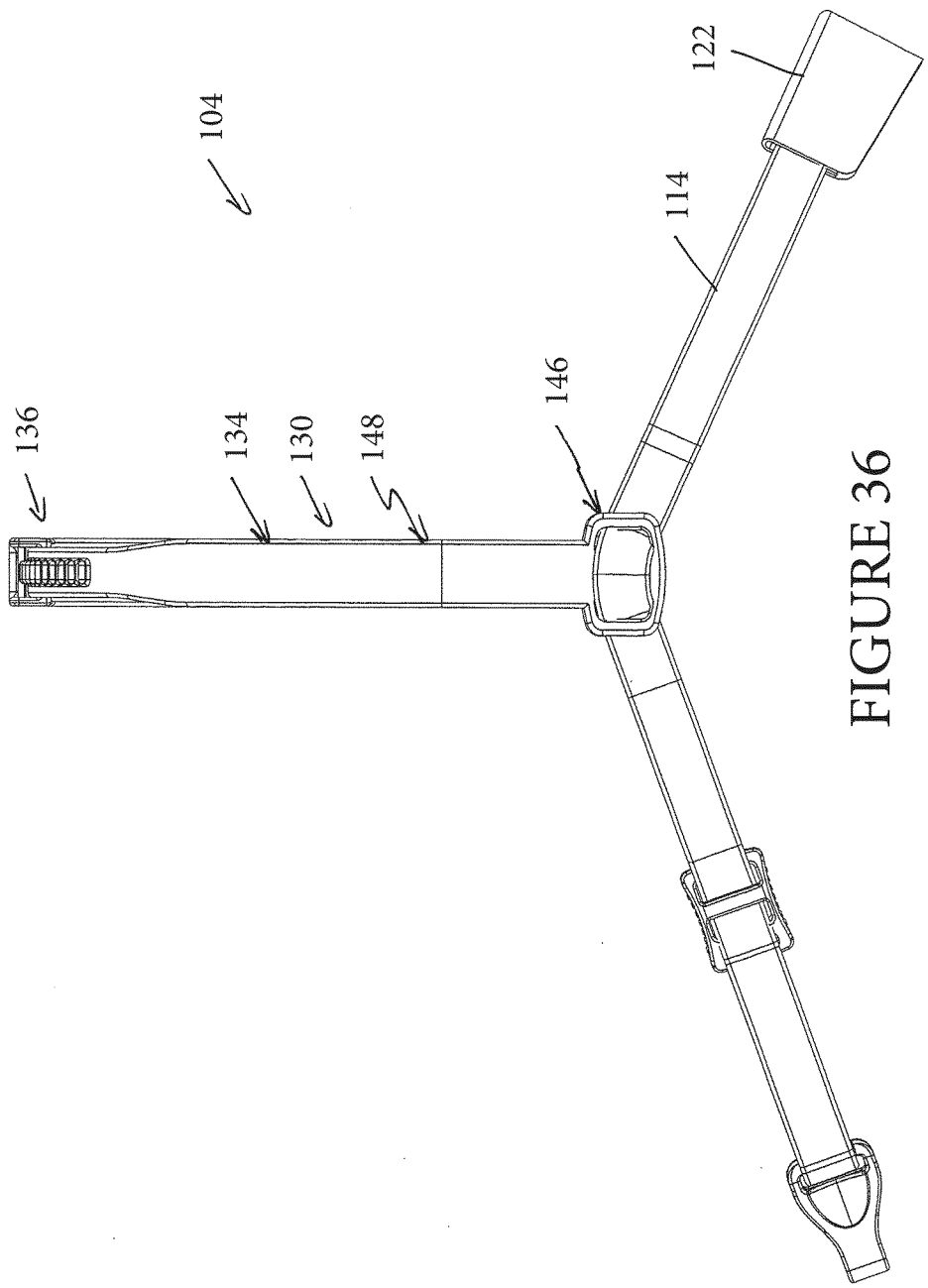
FIG. 36 is a side elevation view of the headgear assembly of FIG. 34.
Figure 37:
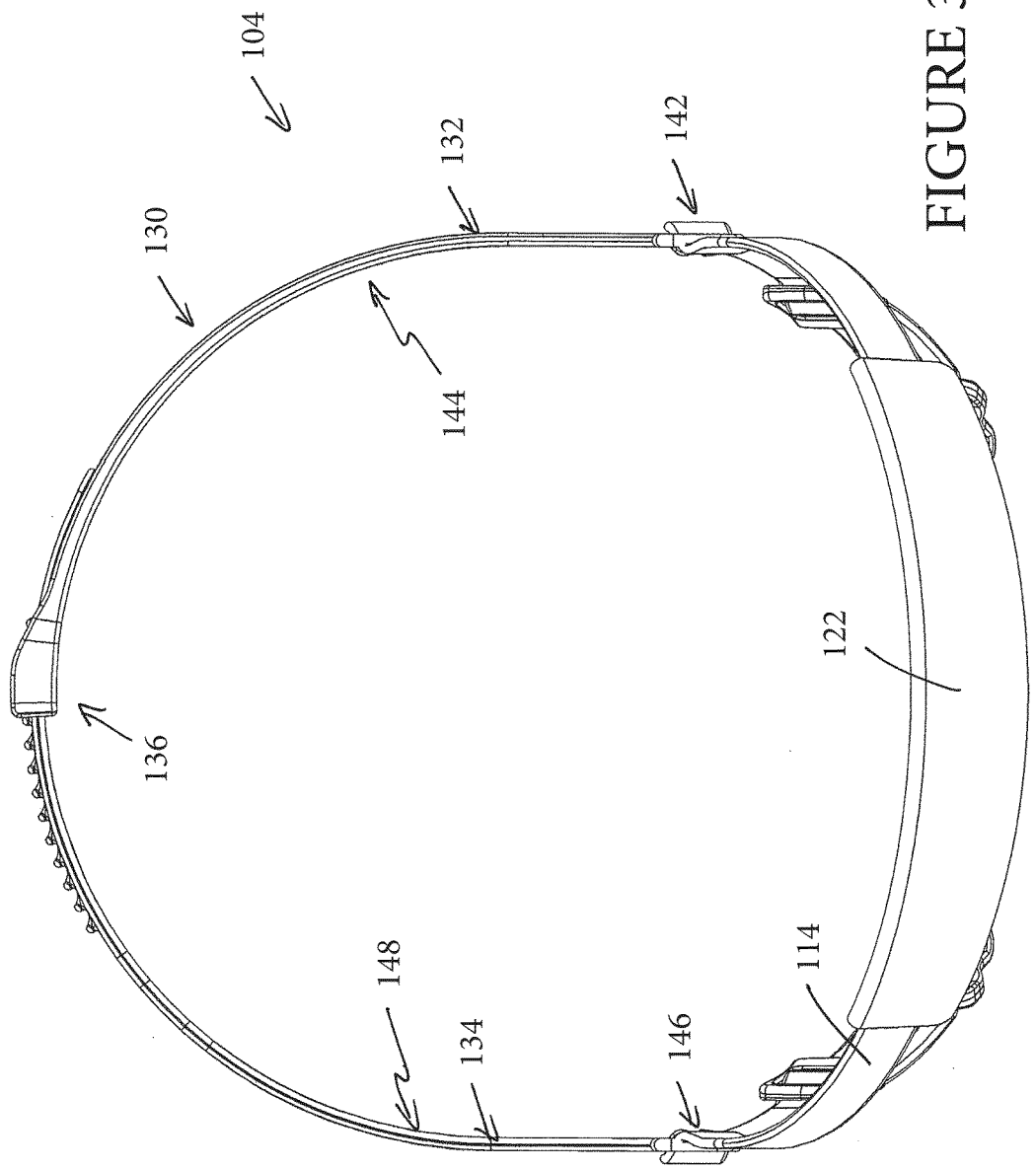
FIG. 37 is a rear elevation view of the headgear assembly of FIG. 34.
Figure 38:
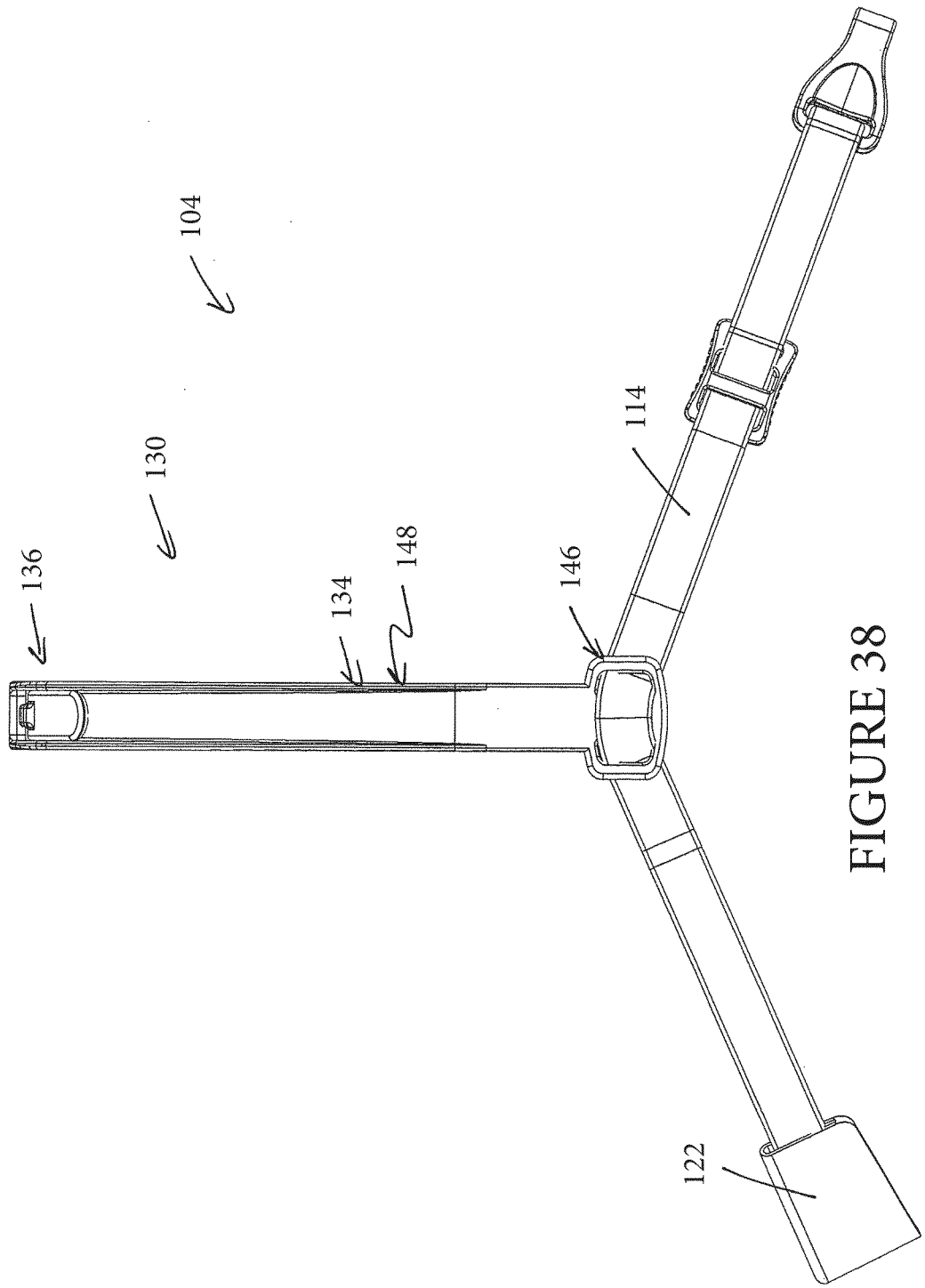
FIG. 38 is a side elevation view of the headgear assembly of FIG. 34.
Figure 39:
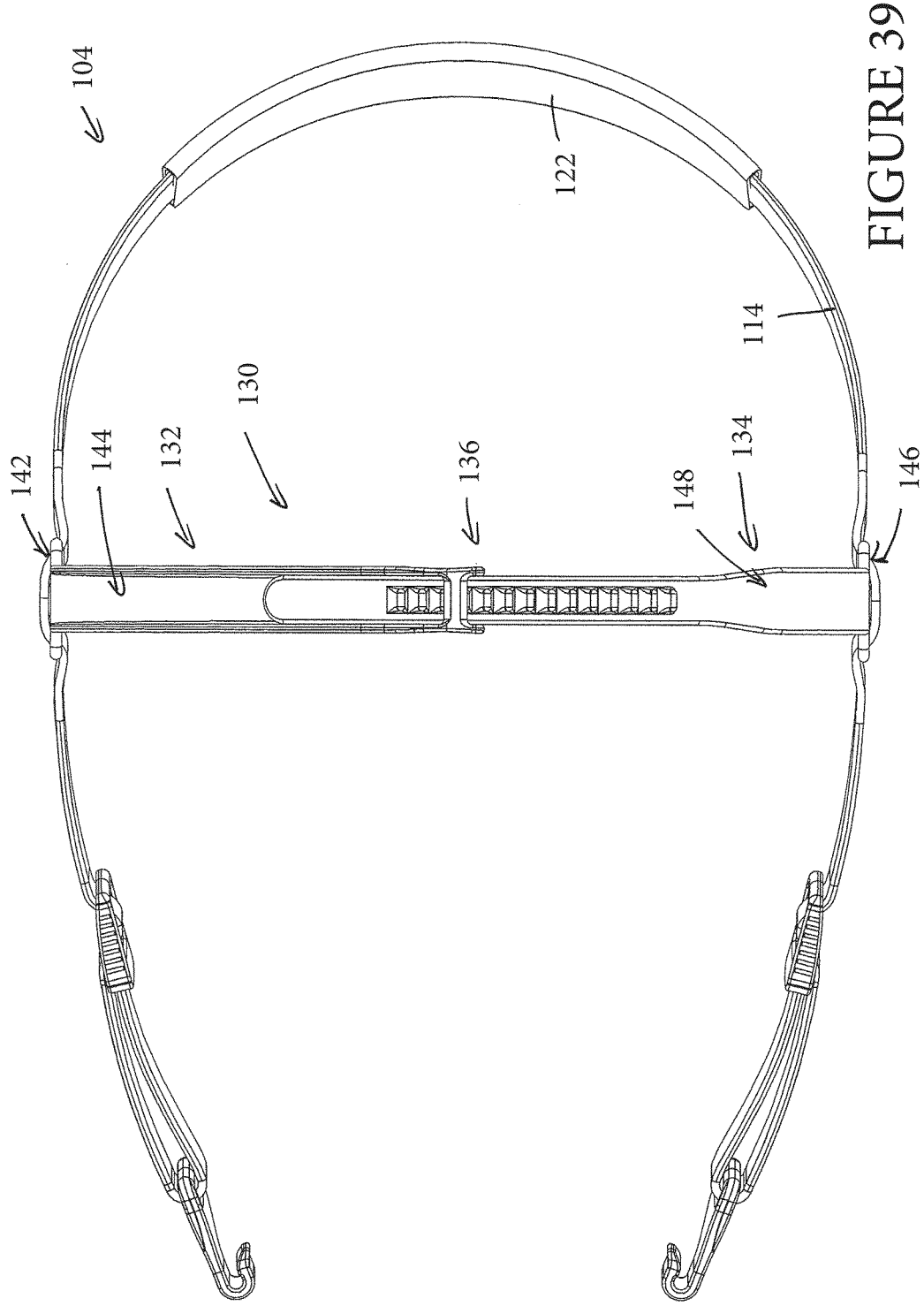
FIG. 39 is a top view of the headgear assembly of FIG. 34.
Figure 40:
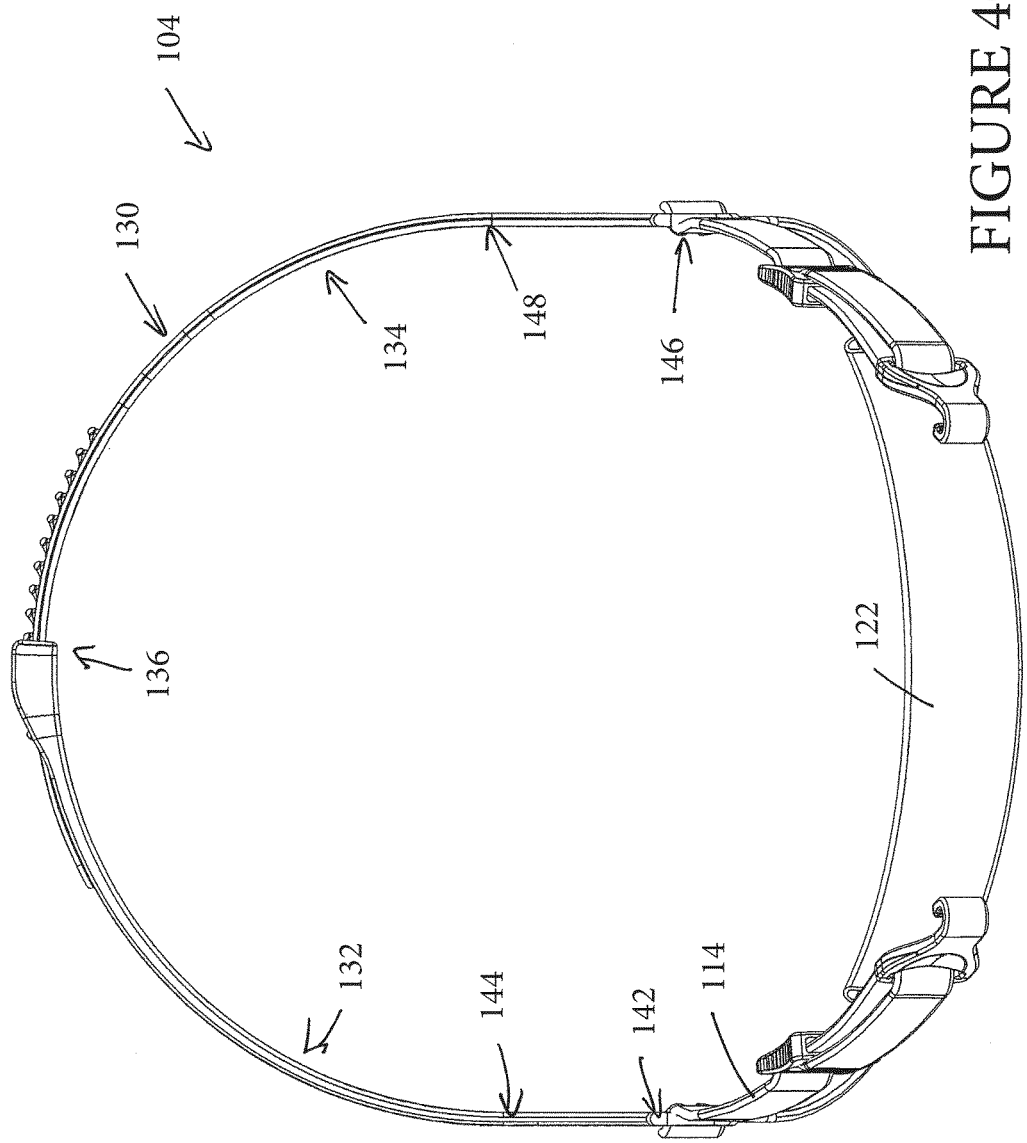
FIG. 40 is a front elevation view of the headgear assembly of FIG. 34.
Figure 41:
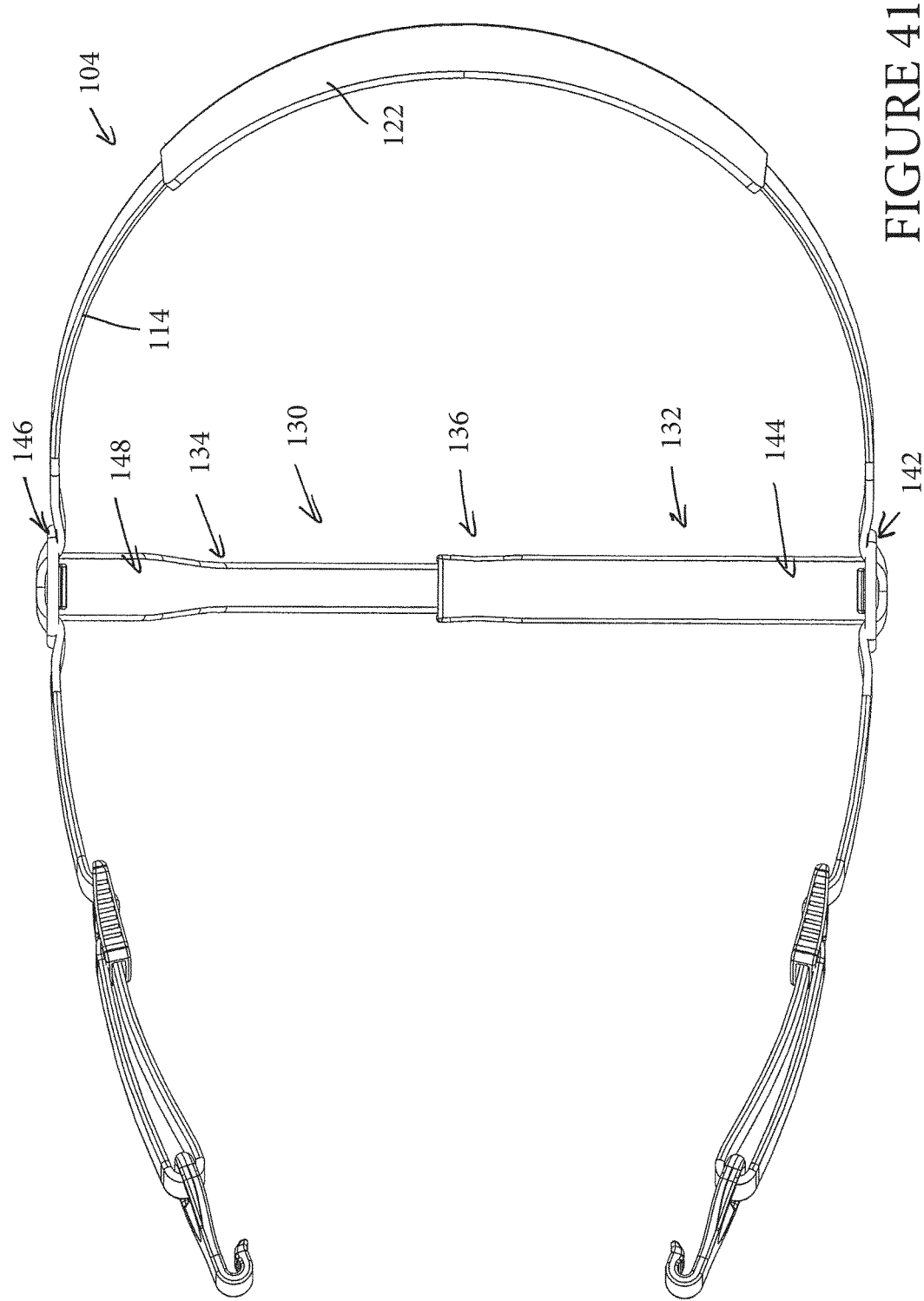
FIG. 41 is a bottom view of the headgear assembly of FIG. 34.
Figure 42:
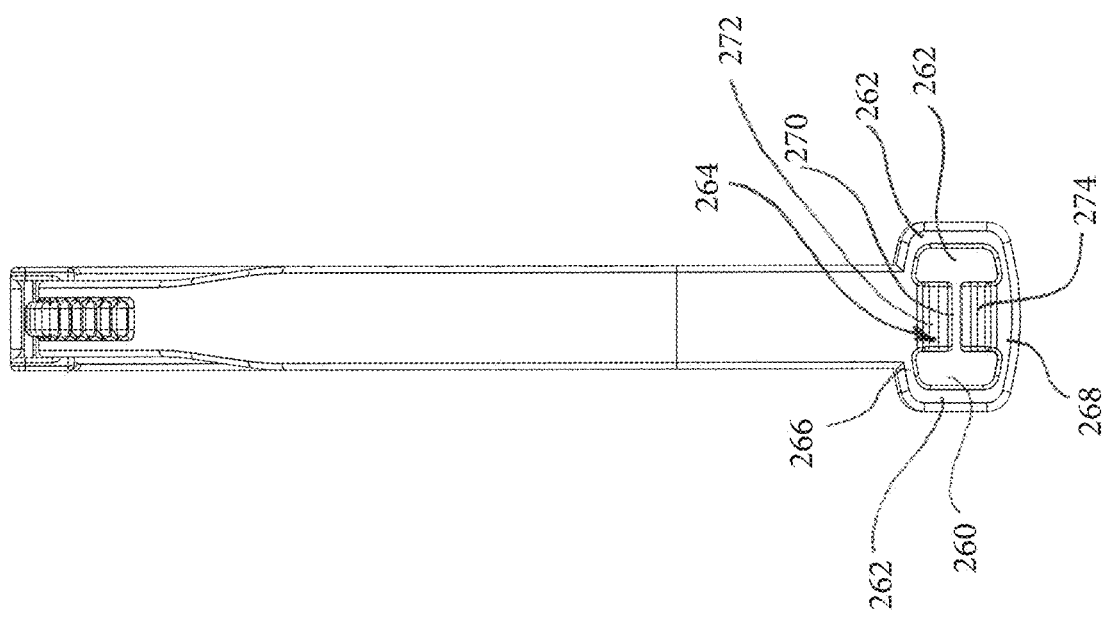
FIG. 42 is a side view of a crown strap assembly of the headgear assembly of FIG. 34.

With reference to FIG. 34, a further adjustment mechanism 136 is illustrated. In the illustrated configuration, the first portion 132 includes a loop 152 that defines a passageway. The second portion 134 can extend into the passageway defined by the loop 152. In the illustrated configuration, the loop 152 can include a tang 232, tab or the like. The tang 232 can extend into the passageway defined by the loop 152. The tang 232 is deflectable and, together with a plurality of ridges or recesses 234, can define a ratchet mechanism 236. The ratchet mechanism 236 can resist expansion of the crown strap assembly 130 while allowing adjustability to shorten the crown strap assembly 130. In some configurations, with enough force applied to the first portion 132 and the second portion 134, the crown strap assembly 130 can be lengthened by overpowering the ratchet mechanism 236. In some configurations, a release can be provided to move the tang 232 and allow lengthening of the crown strap assembly 130. Other configurations can be used keeping in mind a desire for a relatively secure adjustment mechanism, such as any suitable detent arrangement, for example.

The first portion 132 of the crown strap assembly 130 comprises a first bridge region 142 and a first strap region 144. The second portion 134 of the crown strap assembly 130 similarly comprises a second bridge region 146 and a second strap region 148. In some configurations, the first portion 132 and the second portion 134 are generally symmetrical to each other with the exception of the region that defines the adjustment mechanism 136. Other configurations are possible.

Figure 6:
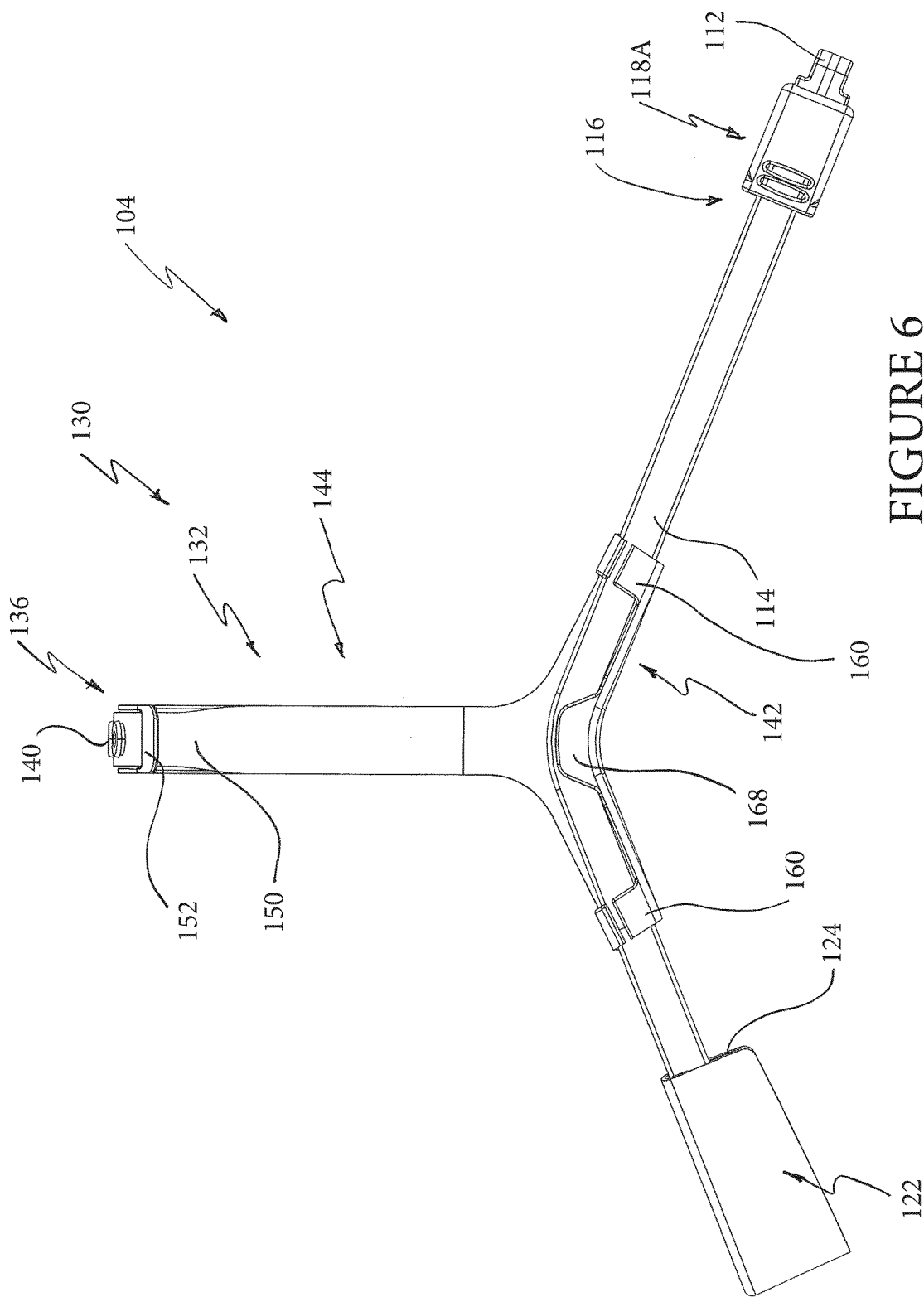
FIG. 6 is a left side view of the headgear of FIG. 1A.
Figure 7:
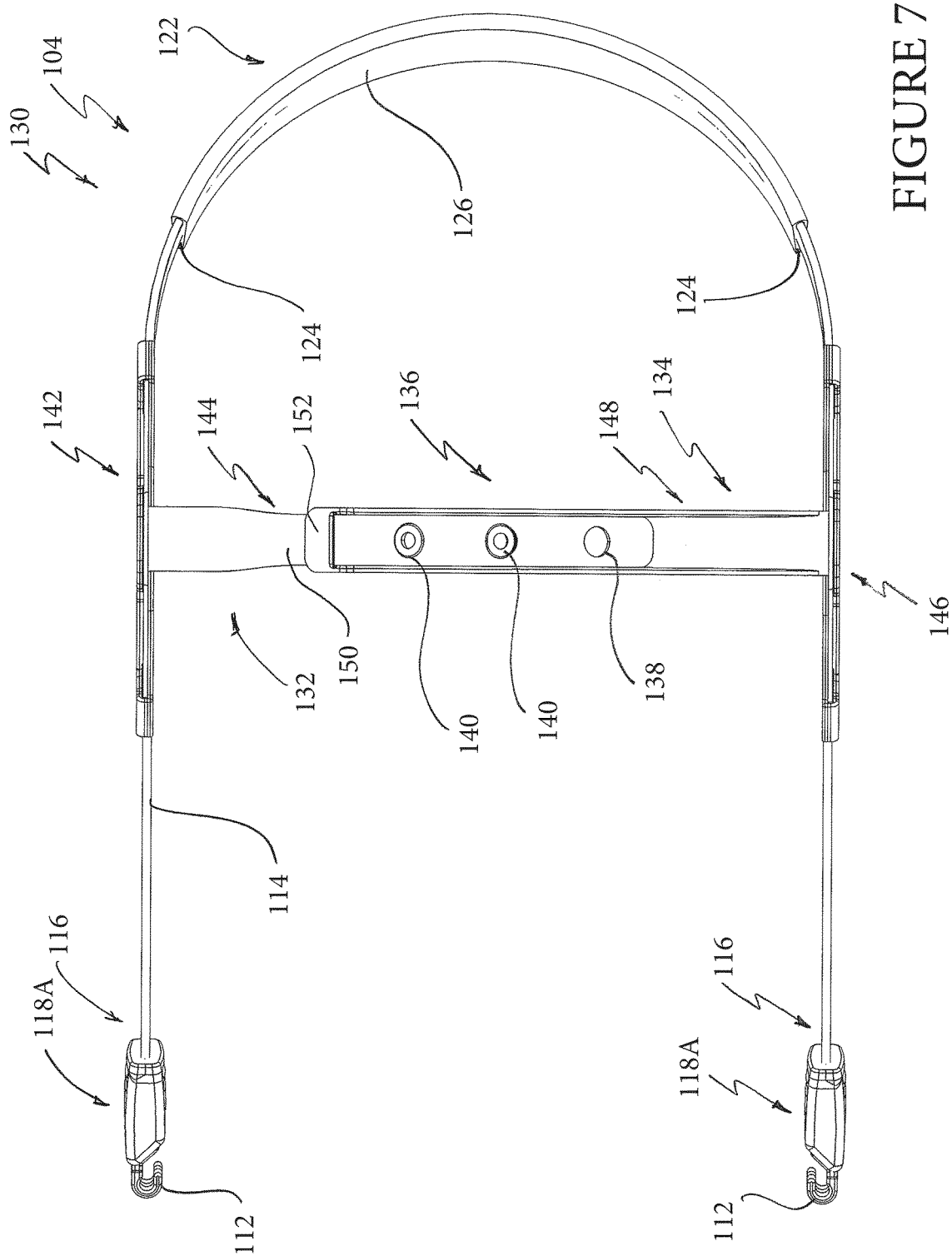
FIG. 7 is a top view of the headgear of FIG. 1A.
Figure 8:
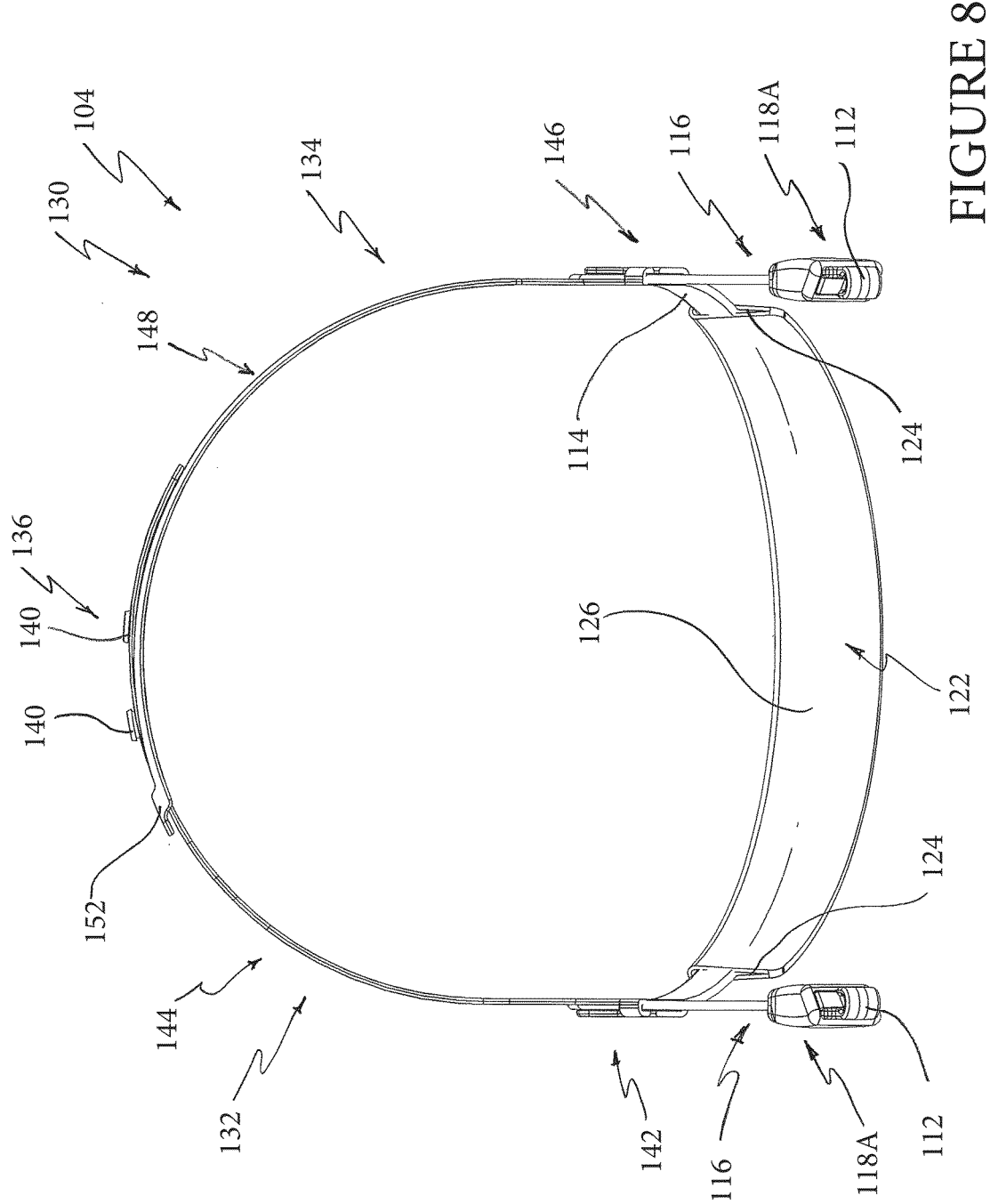
FIG. 8 is a front view of the headgear of FIG. 1A.
Figure 9:
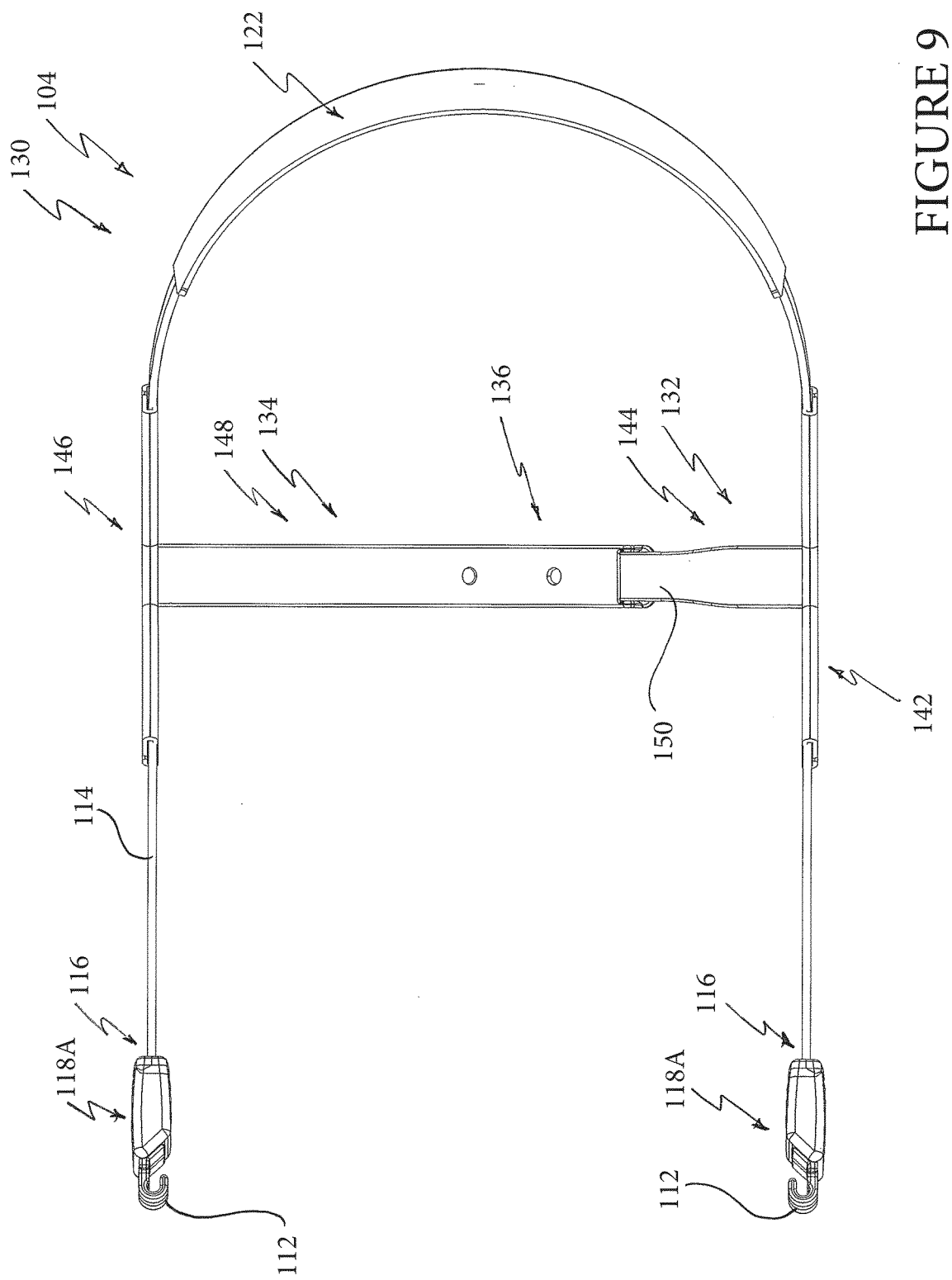
FIG. 9 is a bottom view of the headgear of FIG. 1A.

The first strap region 144 comprises the apertures 138 and, as shown in FIG. 6, may have reduction in width somewhere along its length. In the illustrated configuration, the first strap portion 144 comprises a tapering zone 150 such that a first width of the first strap portion 144 is smaller than a second width of the first strap portion 134 that is closer to the first bridge region 142. The second strap region 148 comprises at least one loop 152. In the illustrated configuration, the loop 152 is positioned at an end of the second strap region 148 furthest from the second bridge region 146. The loop 152 serves to somewhat restrain the first strap region 144 at a location between the posts 140 of the second strap region 148 against significant movement away from the second strap region 148.

In some configurations, the loop 152 defines a passage that has a width. The width of the passage is smaller than the second width of the first strap region 144 and larger than the first width of the first strap region 144. In such configurations, the structure that defines the loop 152 serves to limit the degree to which the first strap region 144 can move along the second strap region 148. Other configurations also are possible. In addition, the location of features on any strap region can be reversed such that elements shown on one strap region can be positioned on the other. For example, the loop 152 is shown on the second strap region 148 in FIG. 1A and the loop 152 is shown on the first strap region in FIGS. 21 and 22.

Figure 10:
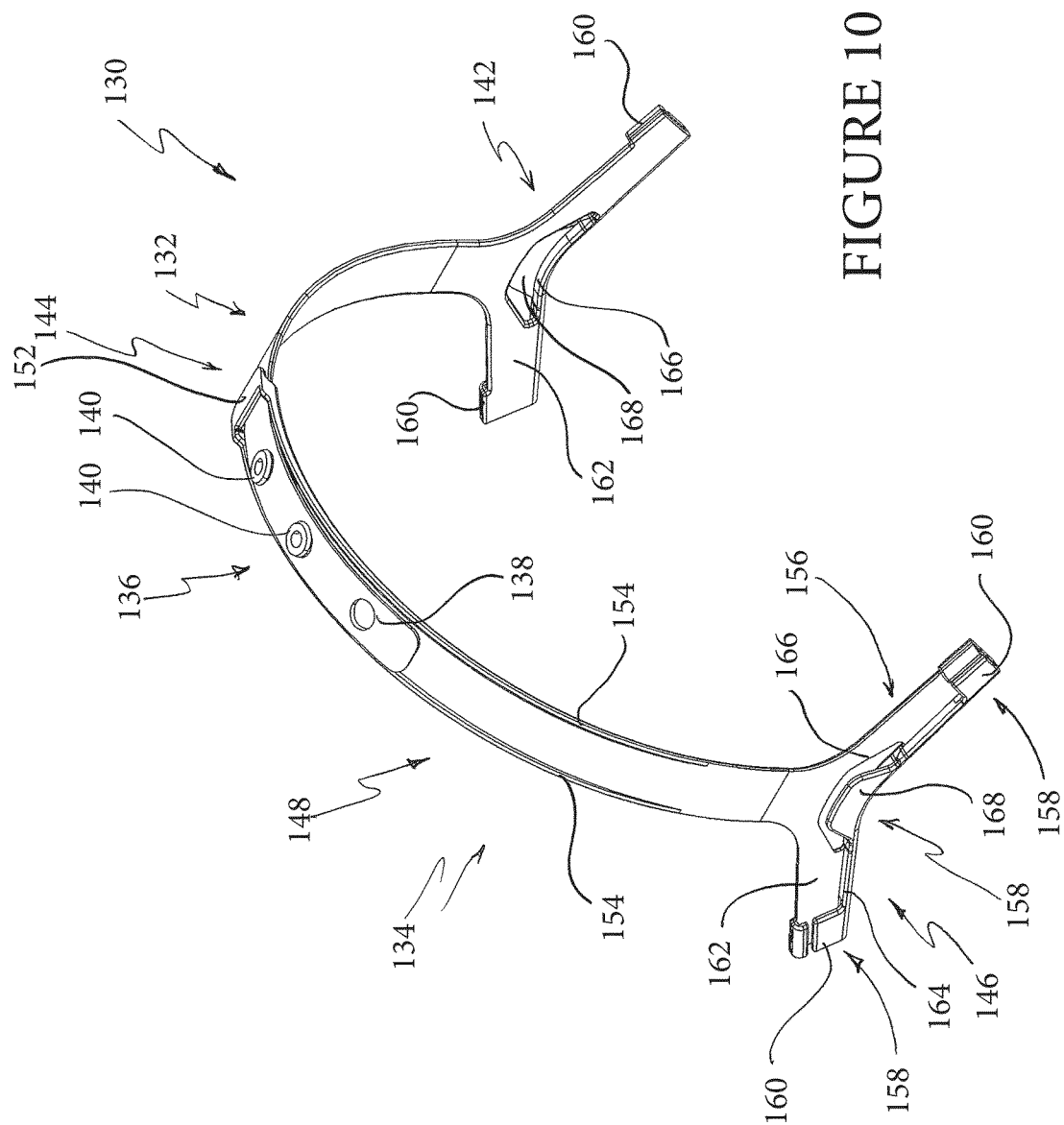
FIG. 10 is a rear perspective of a removable crown strap assembly of the headgear of FIG. 1A.

With continued reference to FIG. 10, the second strap region 148 comprises one or more ribs 154. The illustrated ribs 154 are elongate members that extend along the lateral edge of at least a portion of the second strap region 148. The illustrated ribs 154 extend to and connect with the loop 152. The ribs 154 can taper such that a height of the ribs 154 reduces in a direction away from the loop 152. The narrower portion of the first strap region 144 can fit between the ribs 154. In some configurations, the ribs 154 in the region that will receive the first strap region 144 can be commensurate with the thickness of the first strap region 144. By making the two commensurate, the top of the ribs 154 and the top surface of the first strap region 144 can be generally flush.

With continued reference to FIG. 10, the second bridge region 146 will be described. The first bridge region 142 is generally configured the same as the second bridge region 146. In the illustrated configurations, the first and second bridge regions 142, 146 are generally mirror images of each other. Other configurations are possible.

As described above, the illustrated crown strap assembly 130 is configured for use with a single main strap 114. In some configurations, the main crown strap assembly 130 can be configured to connect with more than one main strap.

In the illustrated configurations, the second bridge region 146 defines a strap passage 156. In some configurations, the passage 156 can be defined by three supporting components 158. The supporting components 158 are spaced apart along a length of the second bridge region 146. In some configurations, two of the three supporting components 158 are configured to secure the main strap 114 against significant upward movement relative to the second bridge region 146 while the third of the three supporting components 158 is configured to secure the main strap 114 against significant downward movement relative to the second bridge region 146. In some configurations, all three of the supporting components 158 are configured to secure the main strap against significant downward movement relative to the second bridge region 146.

With continued reference to FIG. 10, at least two of the three supporting components 158 can define interrupted loops 160. The interrupted loops 160 can include a slotted gap or the like. In the illustrated configuration, the slotted gap or the like can be positioned along an upper portion of the associated loop 160. Each slotted gap can be sized and configured to allow threading of the main strap 114 into the corresponding loop 160. In the illustrated configuration, the loops 160 are flattened loops with two shorter ends connected to two longer ends and the slotted gap is positioned along one of the two longer ends while the other of the longer ends is defined by a main body 162 of the second strap region 148.

The main body 162 of the second bridge region 146 extends between the loops 160 and connects the loops 160 to the second strap region 148. A lower lip 164 extends outward from a lower portion of the main body 162. The lower lip 164 can further resist downward movement of the main strap 114 relative to the second strap region 148. The lower lip 164 can extend outward away from the main body 162 to a degree that generally is commensurate with the outer surface of the loops 160 such that the lower lip 164 and the loops are generally flush with each other. The lower lip 164 can extend between the supporting components 158 and, in some configurations, can fill the spaces between the supporting components 158.

With continued reference to FIG. 10, the main body 162 also defines one or more apertures 166. In the illustrated configuration, the aperture 166 is positioned generally equidistantly to the two ends of the second strap region 148. In some configurations, the aperture 166 is positioned generally equidistantly to the two ends of the main body 162. The aperture 166 can be positioned in the junction between the second strap region 148 and the second bridge region 146. Other configurations are possible.

In the illustrated configuration, the medial member 168 of the three supporting components 158 can at least partially overlap with the aperture 166. In the illustrated configuration, the medial member 168 is positioned fully within a region defined as an extension of the outer bound of the aperture 166 (see FIG. 11). In some configurations, the medial member 168 is positioned such that at least a portion of the aperture extends further toward the ends of the second bridge region 146 relative to the ends of the medial member 168. The medial member 168 can extend upward away from the lower lip 164. The medial member 168 can extend upward away from the lower lip 164 a distance that is at least about one-half of a height of the main strap 114.

Figure 20:
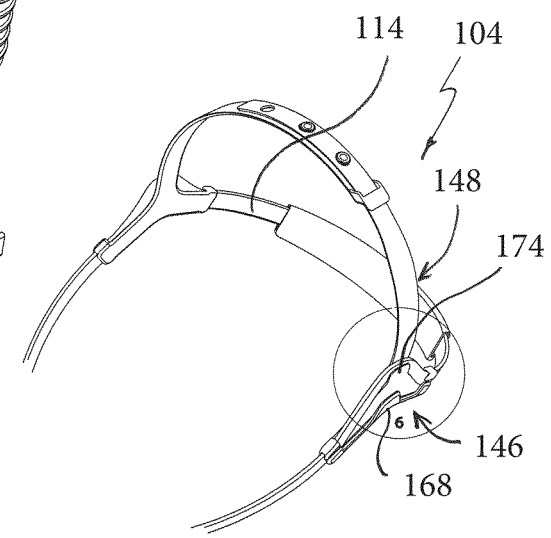
FIG. 20 is a perspective view of a further arrangement for adjusting a rear strap.

In some configurations, such as that shown in FIG. 20, at least one of the bridge region 142, 146 and the associated strap region 144, 148 includes a second medial member 174. The second medial member 174 can be positioned vertical higher than the medial member 168. In some configurations, the second medial member 174 can be positioned vertically above the medial member 168. In some configurations, the second medial member 174 can be sized and configured identically or substantially identically to the medial member 168.

In some configurations, the second medial member 174 can define a strap-accommodating passage between the second medial member 174 and the at least one of the bridge region 142, 146 and the associated strap region 144, 148. The second medial member 174 advantageously provides further adjustability for the headgear assembly 104. The strap 114 can be supported by one of the medial member 168 or the second medial member 174. By moving the strap 114 to the second medial member 174 from the medial member 168, the strap 114 can be effectively shortened. While the illustrated configuration illustrates two medial members 168, 174 on each side of the headgear assembly 104, more than two medial members can be provided on one or both sides of the headgear assembly 104.

Figure 11:
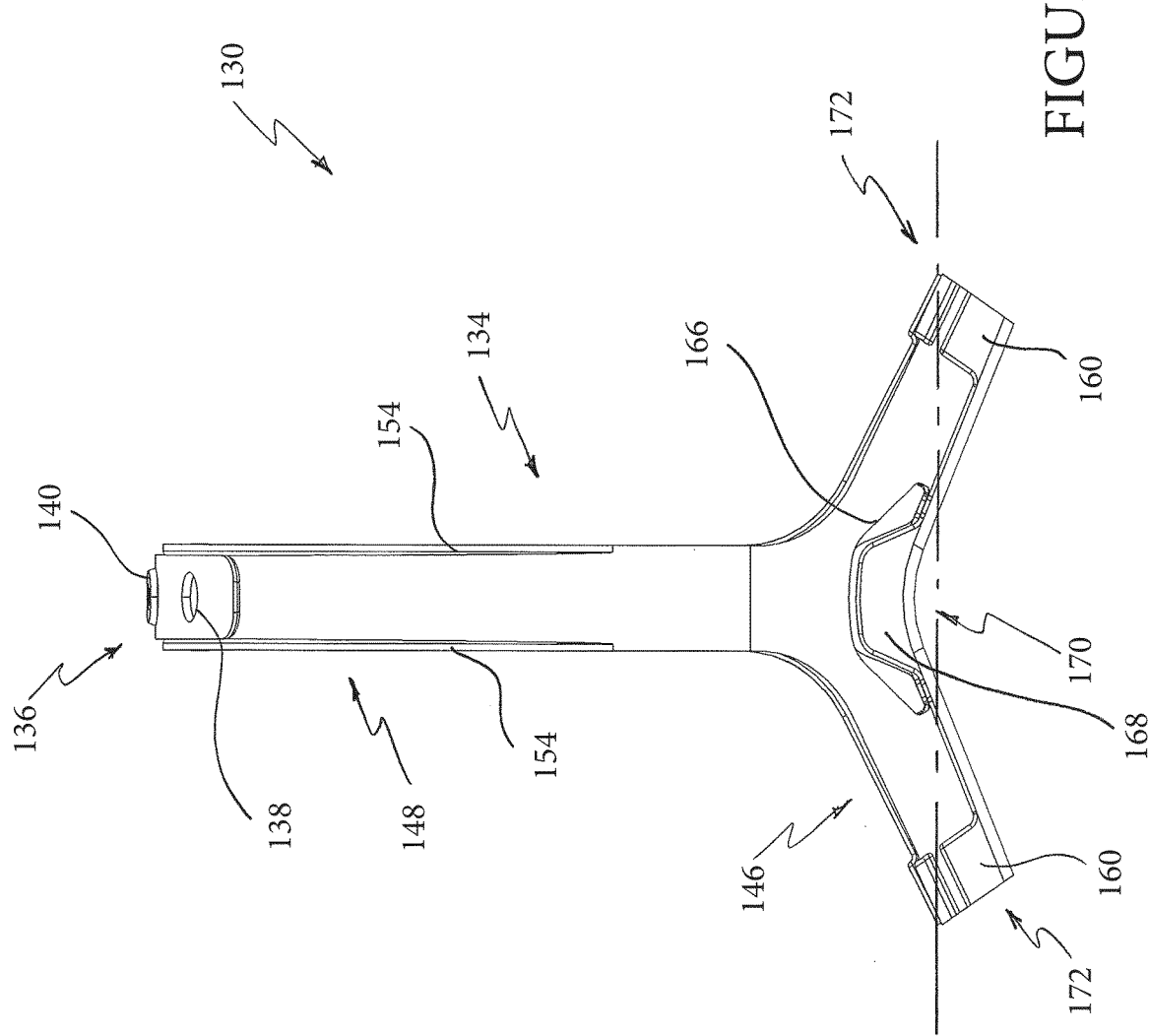
FIG. 11 is a right view of the removable crown strap assembly of FIG. 10.
Figure 12:
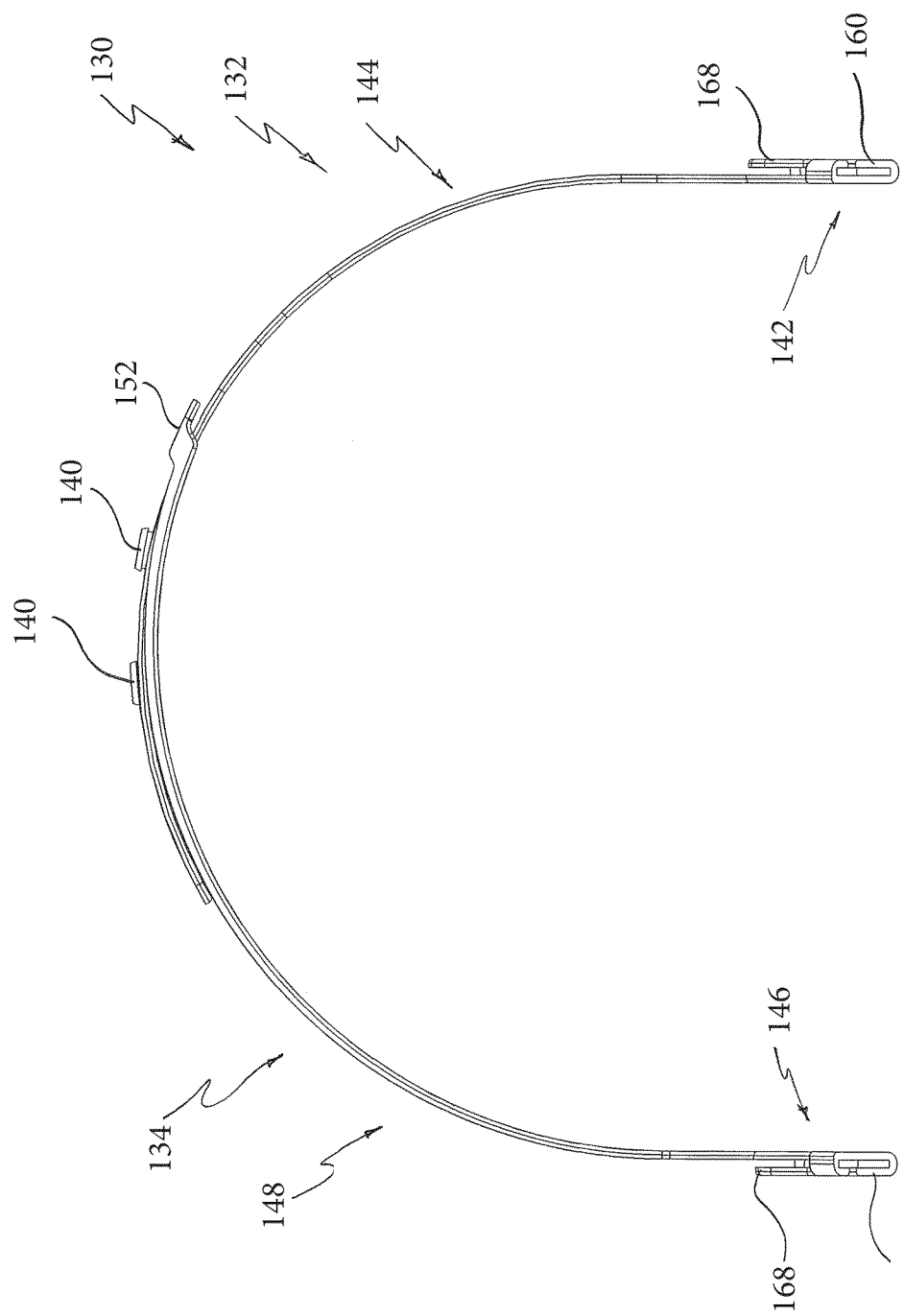
FIG. 12 is a rear view of the removable crown strap assembly of FIG. 10.
Figure 13:
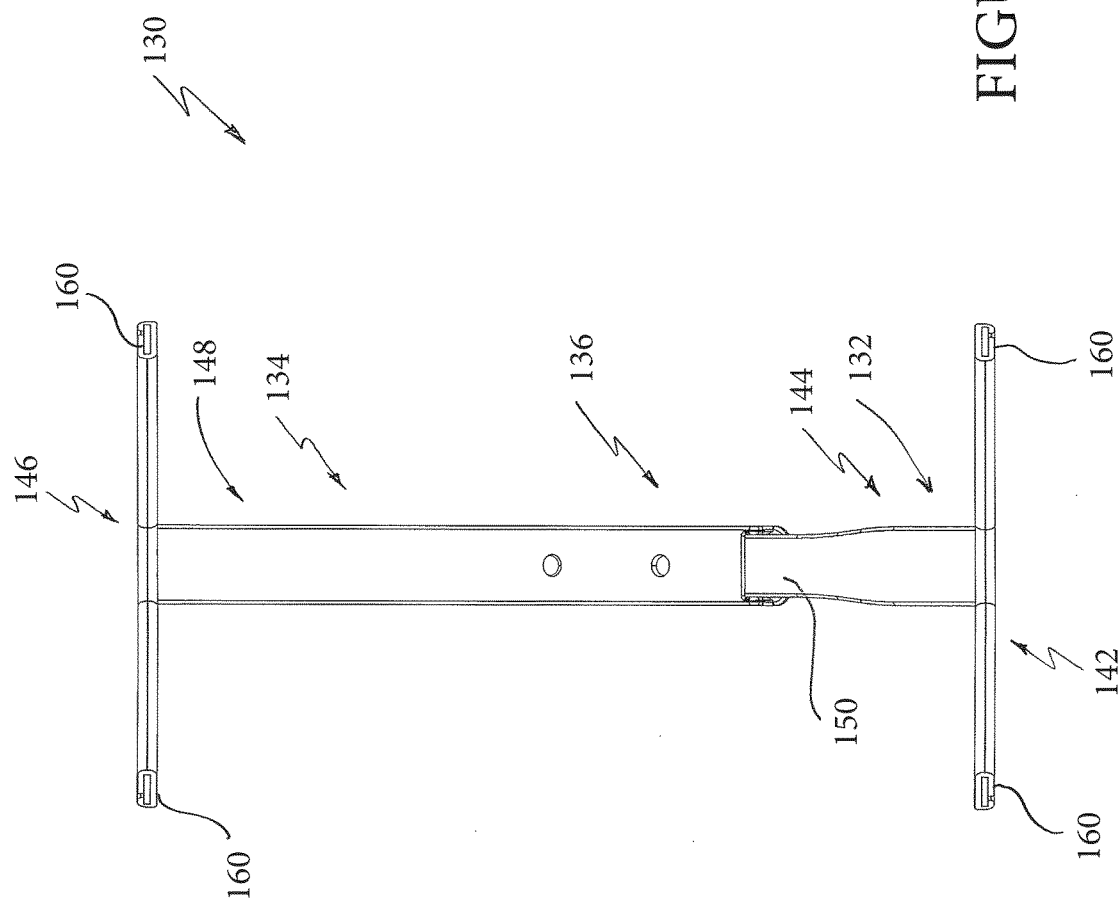
FIG. 13 is a top view of the removable crown strap assembly of FIG. 10.
Figure 16:
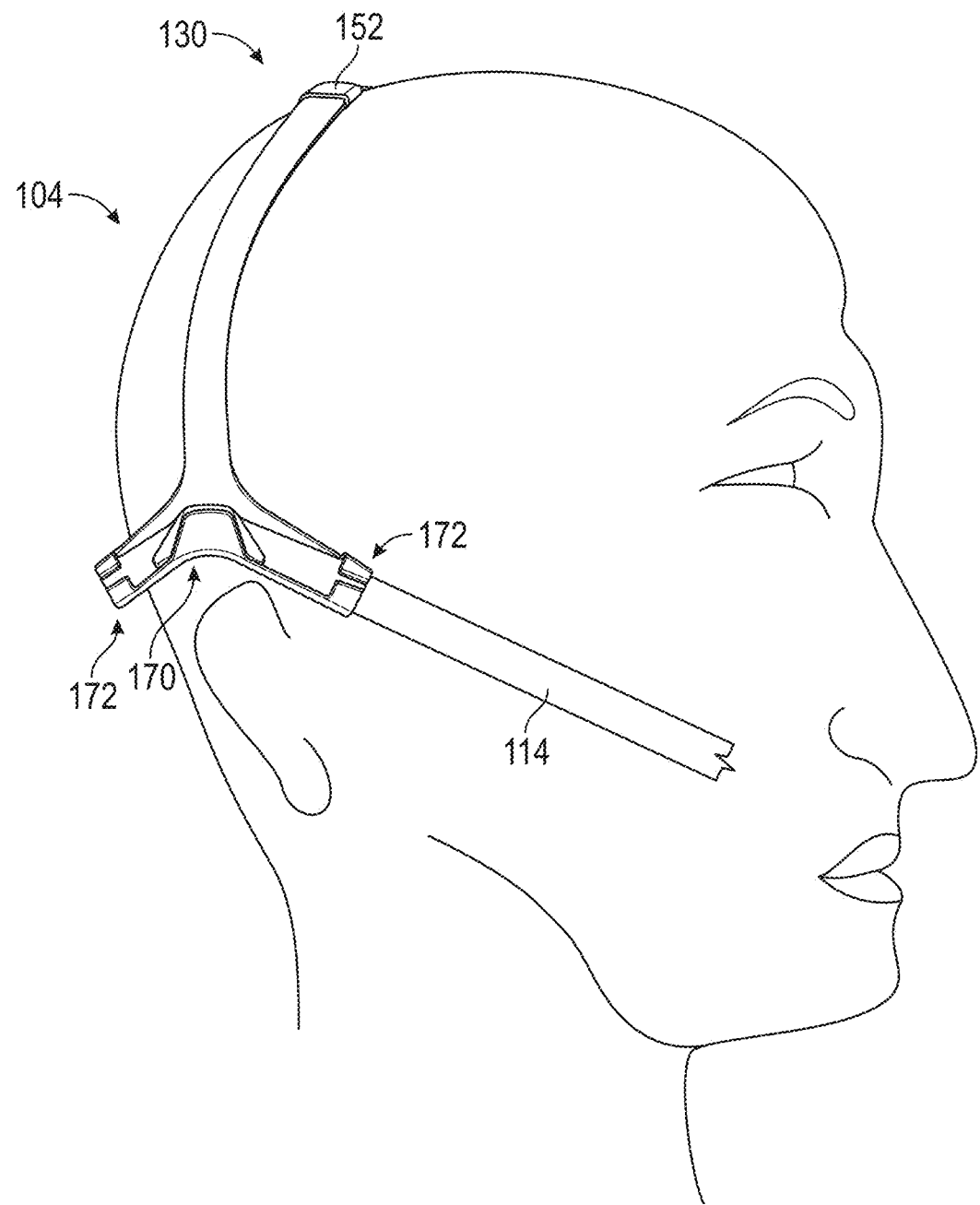
FIG. 16 is a perspective view of the headgear assembly of FIG. 1A shown positioned on a head of a user.

In the illustrated configuration, the second bridge region 146 arcs upward. In other words, as shown in FIG. 11, a central region 170 is vertically higher than ends 172 of the second bridge region 146. In the illustrated configuration, uppermost portions of the ends 172 are positioned lower than a lowermost portion of the central region 170. The second bridge region 146 can be configured such that the top of the ear can be bypassed while maintaining a desired headgear vector for the interface 102 being supported by the headgear. Such an example is illustrated in FIG. 16, for example but without limitation. Moreover, the elongated main body 162 provides arms that reduce pivotal movement of the main strap 114 and the vertical extent of the main body 162 combined with the three supporting components can minimize twisting in the main strap 114. Other configurations are possible.

In use, the main strap 114 can be threaded through the slots in the loops 160 and slid into a gap defined between the medial member 168 and the main body 162 such that the main strap 114 is positioned within the loops 160 and supported by the combination of the main body 162 and the medial member 168. Such a configuration is shown in FIGS. 1-9. In this manner, the user of the headgear can adjust the headgear to a desired configuration by adding the strap, removing the strap or resizing the strap.

With reference to FIGS. 23-33, another configuration for the bridge regions will be described. As illustrated, the headgear assembly 104 comprises the crown strap assembly 130. The crown strap assembly 130 includes the first portion 132 and the second portion 134 that can be secured together in any suitable manner. However, as described above, the crown strap 130 can be a single member or otherwise fixed in length. In the illustrated arrangement, the first portion 132 includes the first bridge region 142 and the first strap region 144. The second portion 132 includes the second bridge region 146 and the second strap region 148. Each of these components can be configured in accordance with any of the description herein.

The first bridge region 142 and the second bridge region 146 can be the same as each other or can be different from each other. In the illustrated configuration, the first and second bridge regions 142, 146 are mirror images of each other. As such, only one will be described but the description applies to each.

The illustrated bridge region 142, 146 defines a passageway that accommodates the strap 114. In some configurations, the passageway is linear. In some configurations, the passageway includes a bend. The some configurations, the passageway includes two linear portions that are connected with a bend.

In the illustrated configuration, the bridge region 142 comprises an inner wall 240 and an outer wall 242 that are connected together. The inner wall 240 and the outer wall 242 generally combine to define a loop that defines the passageway. The inner wall 240 preferably is an extension of the strap region 144, 148 because the inner wall 240 will be adjacent to the head of the user in use.

At least a portion of the loop is interrupted to define an insertion path for the strap 114. In the illustrated configuration, the outer wall 242 includes a slot 244 that interrupts the outer wall 242. The slot 244 is sized, positioned and configured to allow the strap 114 to be threaded into position within the passageway. The slot 244 can be generally straight or horizontal. In some configurations, the slot 244 can be slightly arcuate. In some configurations, the slot 244 can be slightly arcuate with a higher mid-portion than the outer portions. In some configurations, the inner wall may be interrupted. In some configurations, an upper or lower portion of the loop may be interrupted. However, by interrupting the inner wall 240 or the outer wall 242, the slot 244 can be positioned along the longer surface of the strap while also allowing the strap 114 to be secured in the vertical directions (i.e., up and down along the user's head).

Figure 33:
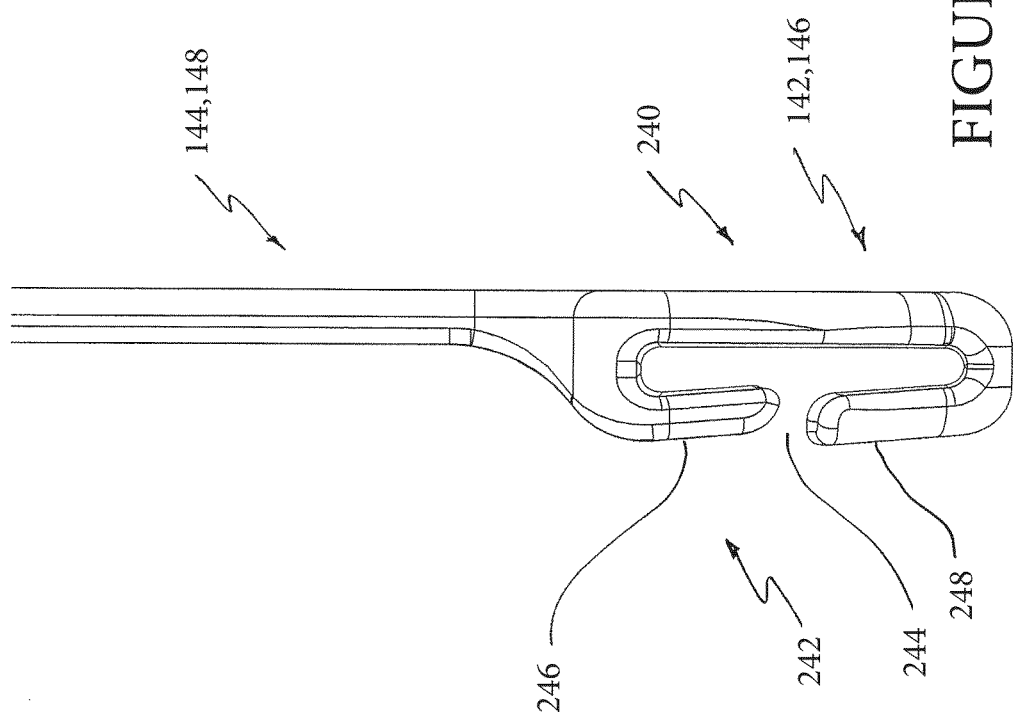
FIG. 33 is an enlarged view of a portion of the crown strap assembly of FIG. 31.

With reference now to FIG. 33, the outer wall 242, as a result of the slot 244, includes an upper portion 246 and a lower portion 248 in the illustrated configuration. In some configurations, the upper portion 246 is slightly less open than the lower portion 248. In other words, the distance between the outer wall 242 and the inner wall 240 is greater at the lower portion 248 than at the upper portion 246. Moreover, in the illustrated configuration, the gap that defines the passageway for the strap 114 is larger at the lower portion 248 than at the upper portion 246. Such a configuration assists in assembly of the strap 114 into the slot 244 and/or help in retention of the strap 114 within the slot 244.

With reference now to FIGS. 34-45, a further configuration for the bridge regions will be described. As illustrated, the headgear assembly 104 comprises the crown strap assembly 130. The crown strap assembly 130 includes the first portion 132 and the second portion 134 that can be secured together in any suitable manner. The first portion 132 includes the first bridge region 142 and the first strap region 144. The second portion 132 includes the second bridge region 146 and the second strap region 148. Each of these components can be configured in accordance with any of the description herein.

The first bridge region 142 and the second bridge region 146 can be the same as each other or can be different from each other. In the illustrated configuration, the first and second bridge regions 142, 146 are mirror images of each other. As such, only one will be described but the description applies to each.

The illustrated bridge region 142, 146 defines a passageway that accommodates the strap 114. The passageway in the arrangement shown in FIGS. 34-45 differs from the passageways described above. In the arrangement shown in FIGS. 34-45, the passageway is defined by two generally vertical slots 260 (see FIG. 42). The two slots 260 are defined by two outer posts 262 and an intermediate portion 264. The strap 114 can be threaded through the slots 260, which allows adjustment of the location of the crown strap assembly 130 along the strap 114.

Figure 44:
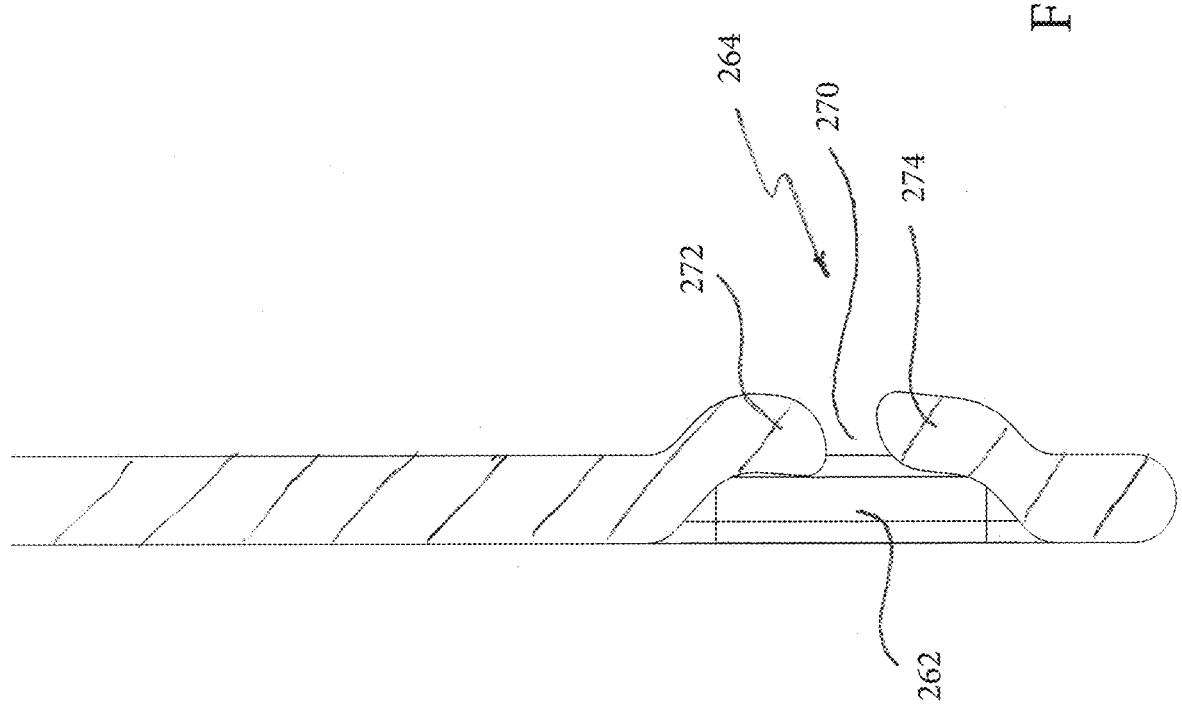
FIG. 44 is an enlarged sectioned view of a portion of the crown strap assembly of FIG. 42.
Figure 45:
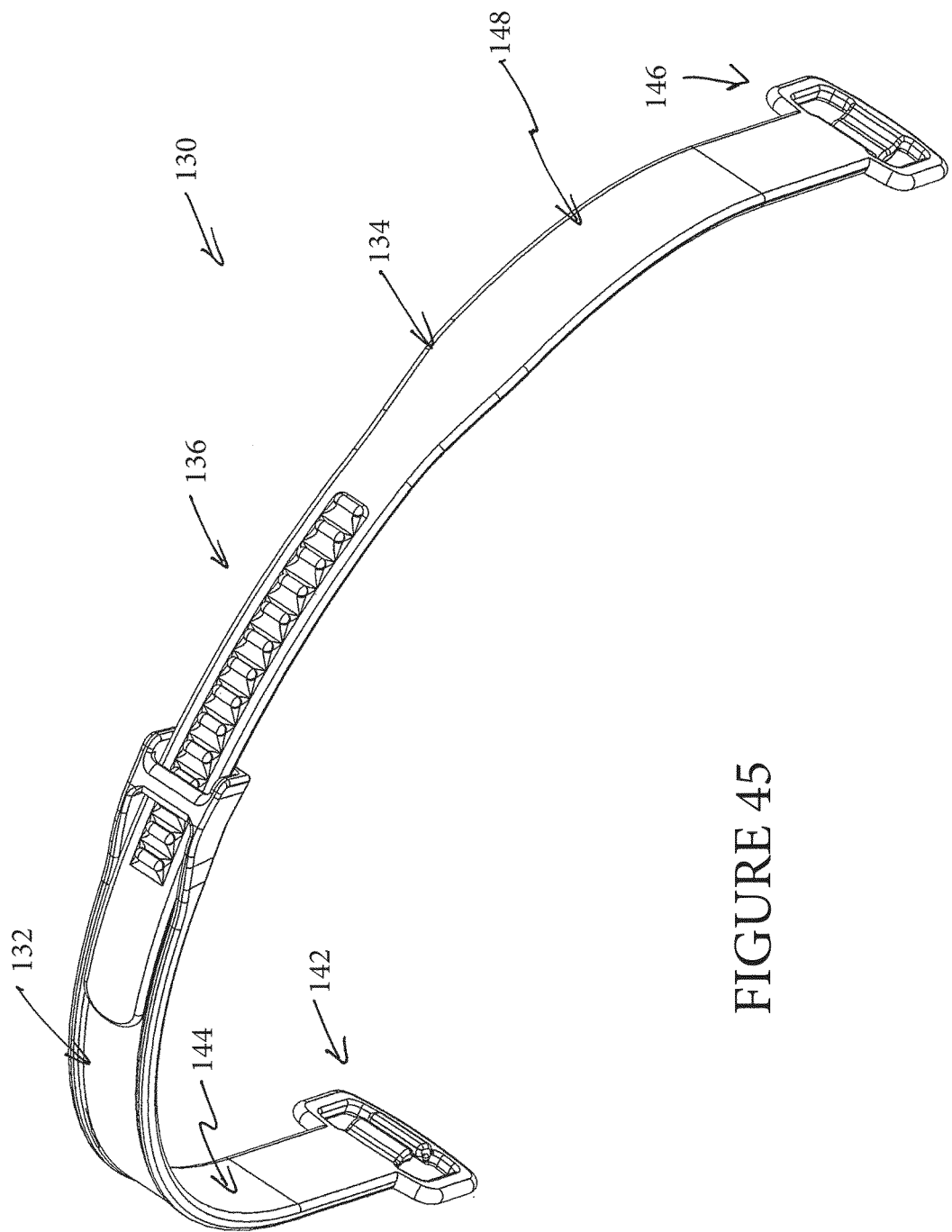
FIG. 45 is a perspective view of the crown strap assembly of FIG. 42.

In the illustrated configuration, the outer posts 262 are connected to each other. The outer posts 262 can be connected with an upper member 266 and a lower member 268. The outer posts 262, upper member 266 and lower member 268 can define a frame into which the strap 114 threads. The frame can be a complete (i.e., gapless) frame. As such, the intermediate portion 264 can be interrupted to enable insertion of the strap 114. In some configurations, one or more of the posts 262 can be interrupted. In some configurations, one or more of the upper member 266 and the lower member 268 can be interrupted. In the illustrated configuration, the intermediate portion 264 is separated into two components by a slot or gap 270. In some configurations, the gap 270 can be positioned such that a single intermediate member is formed. In the illustrated configuration, the gap 270 is positioned such that two intermediate members 272, 274 are formed. In the illustrated configuration, the gap 270 is positioned such that two intermediate members 272, 274 having approximately the same length are formed. Such a configuration is desired for providing a secure connection with the strap 114. Moreover, as shown in FIG. 44, the two intermediate member 272, 274 can have different shapes such that insertion of the strap 114 is made easier. For example, one member may be slightly splayed open relative to the other member, similar to the arrangement illustrated in FIG. 33, for example. In the illustrated configuration, the lower member 274 is splayed open slightly more than the upper member 272. Other configurations are possible.

Figure 43:
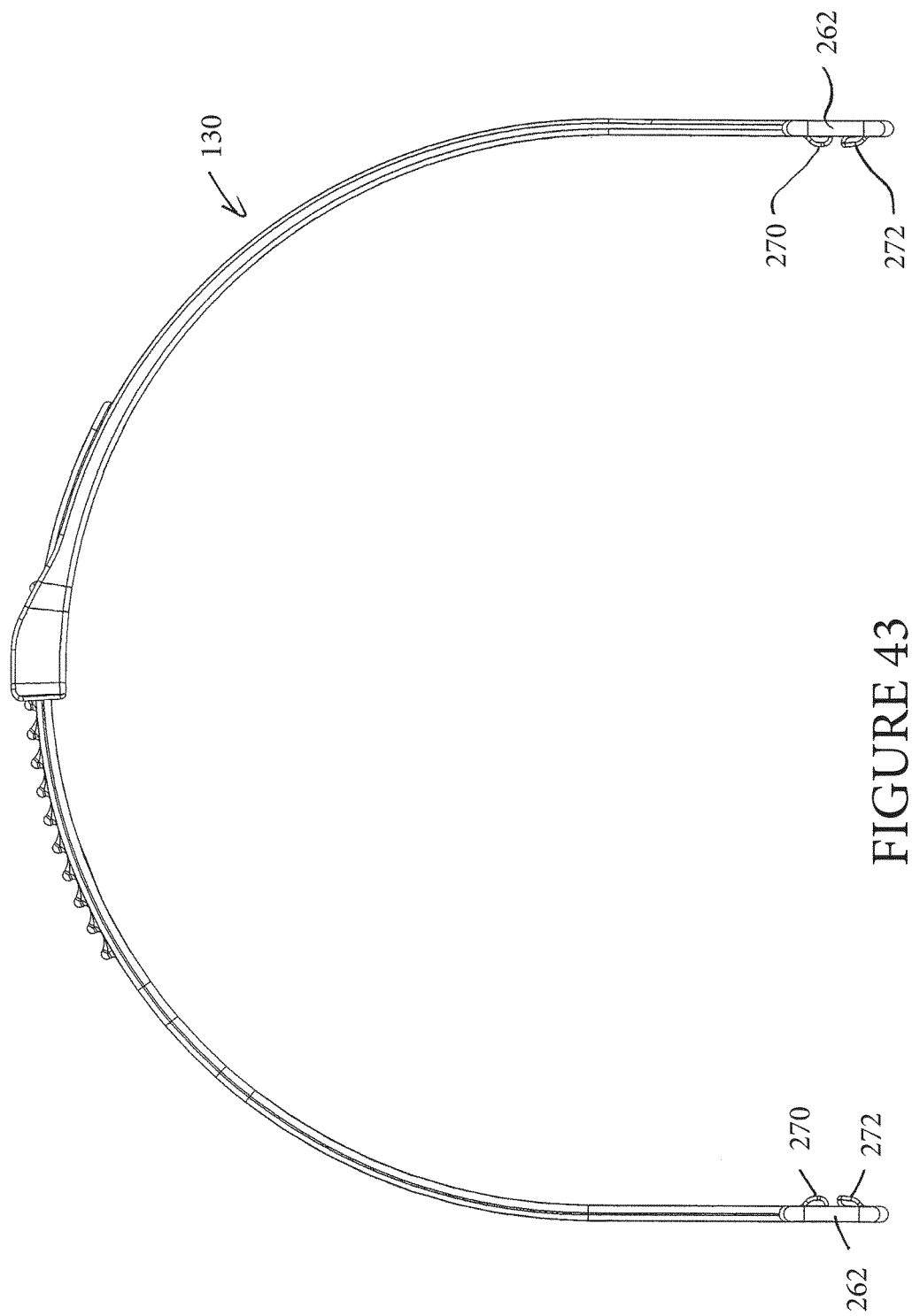
FIG. 43 is a rear view of the crown strap assembly of FIG. 42.

With reference to FIG. 43, the intermediate members 272, 274 can protrude inwardly. In other words, the intermediate members 272, 274 can protrude toward the head of the user in use relative to the outer posts 262, for example. As shown in FIG. 44, the intermediate members 272, 274 can protrude toward the user yet still overlap with the outer posts 262. In some configurations, the intermediate members 272, 274 can be flush with the outer posts 262 on a user-side surface. In some configurations, the intermediate members 272, 274 can protrude outwardly from the outer posts 262 (i.e., away from the user in use). The illustrated configuration facilitates insertion of the strap 114 through the gap 270 and into position relative to the intermediate portion 264.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavor in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. An interface and headgear assembly comprising:
an interface comprising a frame and a seal supported by the frame;
a headgear assembly removably connected to the interface, the headgear assembly comprising a first strap configured to connect at a first end to the interface and at a second end to the interface, a crown strap connected to the first strap, the crown strap comprising a first bridge region and a second bridge region, the first bridge region defining a first passage that receives the first strap and the second bridge region defining a second passage that receives the first strap, wherein each of the first bridge region and the second bridge region is adjustable in position relative to the first strap, wherein each of the first end and the second end is connected to a corresponding hook configured to connect to the interface,
wherein one of the corresponding hooks is an adjustable hook member that allows a length of the first strap to be adjusted through a telescoping mechanism,
wherein the telescoping mechanism comprises an outer sleeve member and an inner arm, the outer sleeve member receiving and obscuring all of the inner arm exclusive of any portion of the inner arm that has been extended outward from the outer sleeve member in a telescoping extension, and squeezing the outer sleeve member permits the inner arm to translate relative to the outer sleeve member;
wherein the first strap forms a single strap that extends uninterrupted between the first end and the second end and is configured to allow the first bridge region and the second bridge region to move along the single strap such that the headgear assembly is adjustable; and
wherein the inner arm is secured against extension and retraction relative to the outer sleeve member unless the outer sleeve member is being squeezed to release the outer sleeve member from the inner arm.

2. The interface and headgear assembly of claim 1, wherein each of the first bridge region and the second bridge region comprises multiple supporting components configured to secure the first bridge region and the second bridge region, respectively, to the first strap.

3. The interface and headgear assembly of claim 2, wherein the multiple supporting components comprise a first loop and a second loop configured to receive the first strap of the interface and headgear assembly.

4. The interface and headgear assembly of claim 3, wherein each of the first loop and the second loop is an interrupted loop.

5. The interface and headgear assembly of claim 4, wherein each of the first loop and the second loop comprises an upper portion and a lower portion defining a slot therebetween.

6. The interface and headgear assembly of claim 5, wherein a width of a passageway defined by each of the first loop and the second loop is smaller at the upper portion than at the lower portion.

7. The interface and headgear assembly of claim 1, wherein the first strap is constructed from a stretchable material.

8. The interface and headgear assembly of claim 7, wherein the crown strap is constructed from a substantially non-stretchable material.

9. The interface and headgear assembly of claim 8, wherein at least a strap region of the crown strap is constructed from a flexible material.

10. The interface and headgear assembly of claim 9, wherein the strap region has sufficient rigidity such that it is capable of substantially maintaining its shape.

11. An interface and headgear assembly comprising:
an interface comprising a mask frame;
a headgear assembly removably connected to the interface, the headgear assembly comprising a main strap, the main strap comprising a first end and a second end, wherein each of the first end and the second end is connected to a corresponding hook configured to connect to the interface, and wherein one of the corresponding hooks is an adjustable hook member that allows a length of the main strap to be adjusted through a telescoping mechanism, wherein the telescoping mechanism comprises an outer sleeve member and an inner arm, the outer sleeve member receiving and obscuring all of the inner arm exclusive of any portion that extends beyond the outer sleeve member in a telescoping extension movement, and squeezing the outer sleeve member permits the inner arm to translate relative to the outer sleeve member;

wherein the main strap forms a single strap that extends uninterrupted between the first end and the second end; and wherein the inner arm is secured against extension and retraction relative to the outer sleeve member unless the outer sleeve member is being squeezed to release the outer sleeve member from the inner arm.

12. The interface and headgear assembly of claim 11, wherein the other of the corresponding hooks is an adjustable hook member that allows the length of the main strap to be adjusted through a telescoping mechanism.

13. The interface and headgear assembly of claim 11, wherein the outer sleeve member is secured to the main strap and the inner arm is secured to the adjustable hook member.

14. The interface and headgear assembly of claim 11, wherein the outer sleeve member defines an inner passage.

15. The interface and headgear assembly of claim 14, wherein the inner passage includes one or more ridges.

16. The interface and headgear assembly of claim 14, wherein the outer sleeve member has recesses on the inner passage and the inner arm includes ridges.

17. The interface and headgear assembly of claim 11, wherein each of the corresponding hooks joins to a post on the mask frame to connect the headgear assembly to the mask frame.

18. The interface and headgear assembly of claim 11, wherein the headgear assembly further comprises a crown strap assembly.

19. The interface and headgear assembly of claim 18, wherein the crown strap assembly is detachable from the main strap.

20. The interface and headgear assembly of claim 11, wherein the main strap is formed of a stretchable material.

21. An interface and headgear assembly comprising:

an interface comprising a mask frame;

a headgear assembly removably connected to the interface, the headgear assembly comprising a main strap, the main strap comprising a first end and a second end, wherein each of the first end and the second end is connected to a corresponding hook configured to connect to the interface, and wherein one of the corresponding hooks is an adjustable hook member that allows a length of the main strap to be adjusted through a telescoping mechanism, wherein the telescoping mechanism comprises an outer sleeve member and an inner arm, the outer sleeve member receiving and obscuring the inner arm when the inner arm is in a retracted position;

the main strap forms a single strap that extends uninterrupted between the first end and the second end; and wherein the inner arm is secured against extension and retraction relative to the outer sleeve member unless the outer sleeve member is being squeezed to release the outer sleeve member from the inner arm.

\* \* \* \* \*